(12) United States Patent
Yodfat et al.

(10) Patent No.: US 8,814,822 B2
(45) Date of Patent: Aug. 26, 2014

(54) RECIPROCATING DELIVERY OF FLUIDS TO THE BODY WITH ANALYTE CONCENTRATION MONITORING

(75) Inventors: Ofer Yodfat, Maccabim-Reut (IL); Ruthy Kaidar, Haifa (IL); Gali Shapira, Haifa (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 576 days.

(21) Appl. No.: 12/116,546

(22) Filed: May 7, 2008

(65) Prior Publication Data

US 2008/0281290 A1 Nov. 13, 2008

Related U.S. Application Data

(60) Provisional application No. 60/928,054, filed on May 7, 2007.

(51) Int. Cl.
*A61M 31/00* (2006.01)

(52) U.S. Cl.
USPC .......... 604/67; 604/64; 604/66; 604/500; 604/503; 604/890.1; 604/891.1

(58) Field of Classification Search
USPC .......... 604/27, 28, 31, 35, 65–67, 500, 503, 604/890.1, 891.1
See application file for complete search history.

(56) References Cited

U.S. PATENT DOCUMENTS

| | | |
|---|---|---|
| 3,631,847 A | 1/1972 | Hobbs, II |
| 3,771,694 A | 11/1973 | Kaminski |
| 4,544,369 A | 10/1985 | Skakoon |
| 4,657,486 A | 4/1987 | Stempfle |
| 5,957,895 A | 9/1999 | Sage |
| 6,091,976 A * | 7/2000 | Pfeiffer et al. .......... 600/347 |
| 6,391,643 B1 | 5/2002 | Chen |

(Continued)

FOREIGN PATENT DOCUMENTS

| | | |
|---|---|---|
| WO | WO91/16416 | 10/1991 |
| WO | WO2006/103061 | 10/2006 |

(Continued)

OTHER PUBLICATIONS

U.S. Appl. No. 60/837,877, filed Aug. 14, 2006, Ofer Yodfat.

(Continued)

*Primary Examiner* — Quynh-Nhu H Vu
*Assistant Examiner* — Larry R Wilson
(74) *Attorney, Agent, or Firm* — Roche Diagnostics Operations, Inc.

(57) ABSTRACT

A volume of an analyte-enriched fluid can be withdrawn out of a user's subcutaneous compartment using a patch unit that includes a reversible pumping mechanism. The volume can be withdrawn out of the body and into the patch unit through a cannula inserted into the subcutaneous compartment so that an analyte concentration in the volume can be measured using a sensing element within the patch unit. After analyte concentration analysis, at least the volume can be delivered back into the subcutaneous compartment by operating the pumping mechanism in a forward direction. biologically compatible fluid can optionally be pumped into the subcutaneous compartment from a reservoir in the patch unit and then allowed to partially or completely equilibrate with the analyte concentration in the interstitial fluid of the subcutaneous compartment via a permeable or semi-permeable cannula surface before being drawn back into the patch unit for analysis. Related systems, apparatus, methods, and/or articles are also described.

22 Claims, 30 Drawing Sheets

(56) References Cited

U.S. PATENT DOCUMENTS

| | | | |
|---|---|---|---|
| 6,485,461 | B1 | 11/2002 | Mason |
| 6,537,243 | B1 * | 3/2003 | Henning et al. ............... 604/28 |
| 6,558,351 | B1 | 5/2003 | Steil q |
| 6,589,229 | B1 | 7/2003 | Connelley |
| 6,723,072 | B2 | 4/2004 | Flaherty |
| 6,740,059 | B2 | 5/2004 | Flaherty |
| 6,892,085 | B2 | 5/2005 | McIvor |
| 6,975,893 | B2 | 12/2005 | Say |
| 2002/0169439 | A1 * | 11/2002 | Flaherty ............... 604/891.1 |
| 2005/0272898 | A1 | 12/2005 | Shah |
| 2006/0079809 | A1 | 4/2006 | Goldberger |
| 2006/0189858 | A1 | 8/2006 | Sterling |
| 2006/0224109 | A1 * | 10/2006 | Steil et al. ............... 604/66 |
| 2007/0106218 | A1 | 5/2007 | Yodfat |
| 2008/0215035 | A1 | 9/2008 | Yodfat |
| 2009/0198215 | A1 * | 8/2009 | Chong et al. ............... 604/506 |

FOREIGN PATENT DOCUMENTS

| | | | |
|---|---|---|---|
| WO | WO 2006103061 A1 * | 10/2006 | |
| WO | WO2008/037316 | 4/2008 | |
| WO | WO 2008037316 A2 * | 4/2008 | ............... A61B 5/14 |

OTHER PUBLICATIONS

U.S. Appl. No. 60/833,110, filed Jul. 24, 2008, Ofer Yodfat.

U.S. Appl. No. 11/989,681, filed Jan. 28, 2008, Ofer Yodfat.

UK Prospective Diabetes Study (UKPDS) Group, Intensive blood-glucose control with sulphonylureas or insulin compared with conventional treatment and risk of complications in patients with type 2 diabetes (UKPDS 33); Lancet, 352: 837-853 (1998).

The Diabetes Control and Complications Trial Research Group, "The Effect of Intensive Treatment of Diabetes on the Development and Progression of Long-Term Complications in Insulin-Dependent Diabetes Mellitus", The New England Journal of Medicine, 329(14): 977-986 (1993).

The Diabetes Control and Complications Trial/Epidemiology of Diabetes Interventions and Complications (DCCT/EDIC) Study Research Group, "Intensive Diabetes Treatment and Cardiovascular Disease in Patients with Type 1 Diabetes", The New England Journal of Medicine, 353(25): 2643-2653 (2005).

Roger J. McNichols, et al., "Optical glucose sensing in biological fluids: an overview", Journal of Biomedical Optics, 5(1): 5-16, Jan. 2000.

UK Prospective Diabetes Study Group, "Tight blood pressure control and risk of macrovascular and microvascular complications in type 2 diabetes: UKPDS 38", BMJ, 317(7160): 703-713 (1998).

J. Bolinder et al., "Microdialysis measurement of the absolute glucose concentration in subcutaneous adipose tissue allowing glucose monitoring in diabetic patients", Diabetologia, 35:1177-1180 (1992).

Janet A. Tamada et al., "Noninvasive Glucose Monitoring Comprehensive Clinical Results", Journal of the American Medical Association, 282: 1839-1844 (1999).

John J. Mastrototaro, "The MiniMed Continuous Glucose Monitoring System", Diabetes Technology & Therapeutics, vol. 2, Supplement 1: 13-18 (2000).

T.I. Valdes et al., "In Vitro and In Vivo Degradation of Glucose Oxidase Enzyme Used for an Implantable Glucose Biosensor", Diabetes Technology & Therapeutics, 2(3): 367-376 (2000).

Alberto Maran et al., "Continuous Subcutaneous Glucose Monitoring in Diabetic Patients", Diabetes Care, 25: 347-352 (2002).

Iris M. Wentholt et al., "Comparison of a Needle-type and a Microdialysis Continuous Glucose Monitor in Type 1 Diabetic Patients", Diabetes Care, 28:2871-2876 (2005).

L. Schaupp et al., "Direct access to interstitial fluid in adipose tissue in humans by use of open-flow microperfusion", Am. J. Physiol. Endocrinol. Metab., 276(2): E401-408 (Feb. 1999).

International Search Report and Written Opinion dated Jun. 19, 2009, issued in connection with counterpart PCT application PCT/IB2008/003357.

* cited by examiner

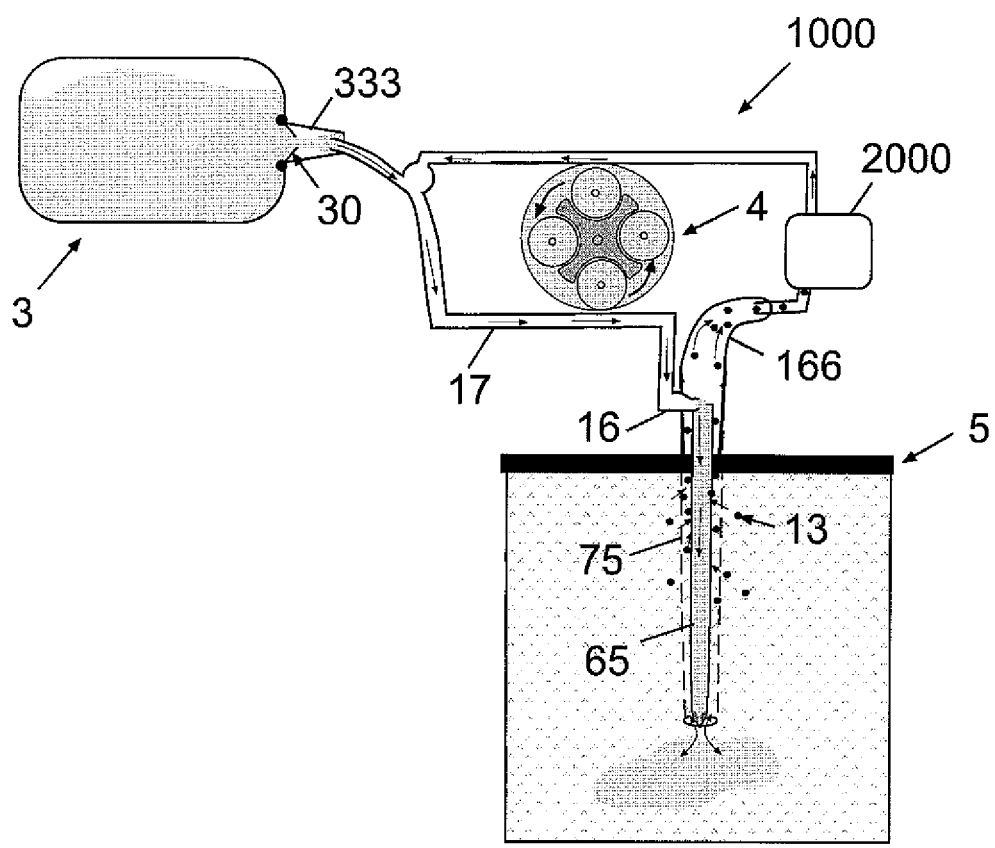
Fig. 29
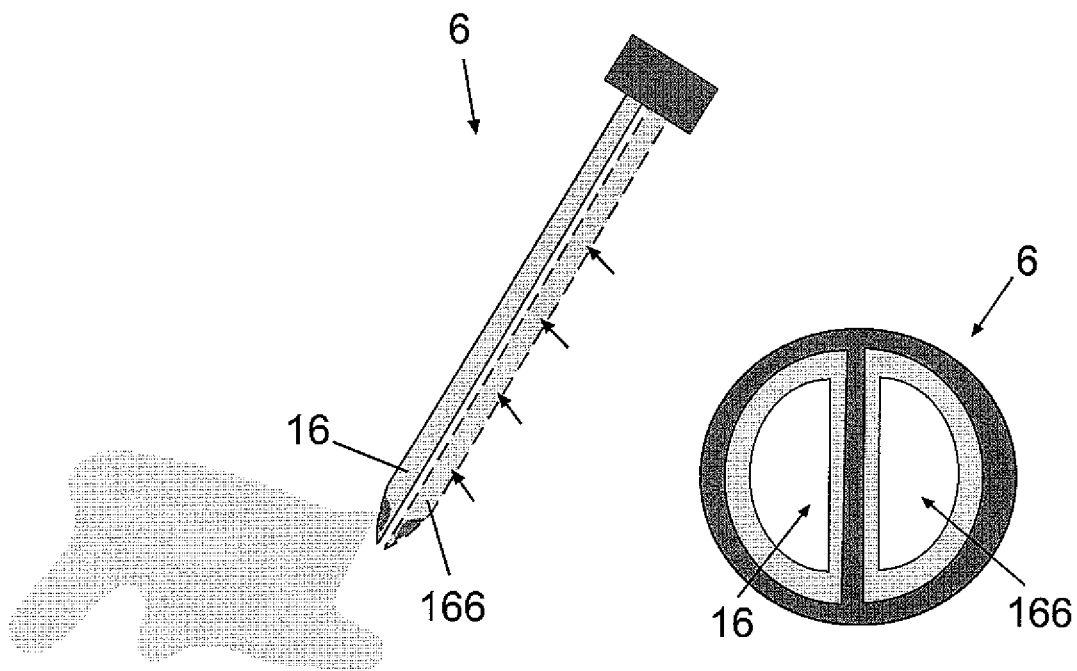
Fig 30a  Fig 30b

RECIPROCATING DELIVERY OF FLUIDS TO THE BODY WITH ANALYTE CONCENTRATION MONITORING

CROSS-REFERENCE TO RELATED APPLICATION

This application claims the benefit of U.S. provisional patent application Ser. No. 60/928,054, filed on May 7, 2007 and entitled "A Reciprocating System for Monitoring Analyte Concentrations and/or Dispensing Fluids into a Body" which is incorporated by reference herein in its entirety.

FIELD

The subject matter described herein relates to monitoring analyte concentrations within the body and dispensing fluids into the body. One or both of these functions can be performed using a reciprocating delivery and analysis apparatus.

BACKGROUND

Diabetes Mellitus is a disease of major global importance that has increased in frequency at almost epidemic rates. The worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels and thus maintain near constant glucose levels in the body.

Much of the burden of the disease to the patient and to health care resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin. [DCCT Trial, *N. Engl. J. Med.* 1993; 329: 977-986, UKPDS Trial, *Lancet* 1998; 352: 837-853. *BMJ* 1998; 317, (7160): 703-13 and the EDIC Trial, *N. Engl. J. Med.* 2005; 353, (25): 2643-53]. Thus, maintaining euglycemia by frequent glucose measurements and adjustment of insulin delivery accordingly is of utmost importance.

In theory, returning blood glucose levels to normal by hormone replacement therapy using insulin injections and/or other treatments in diabetes should prevent complications, but, frustratingly, near-normal blood glucose concentrations are very difficult to achieve and maintain in many patients, particularly those with type 1 diabetes. In these patients, blood glucose concentration can swing between very high (hyperglycemia) and very low (hypoglycemia) levels in an unpredictable manner. Thus, tight glycemic control is required. This control can be achieved by providing a means capable of substituting the two functions of the normal pancreas—glucose monitoring and insulin delivery. Furthermore, a closed loop system provided with a feedback mechanism linking between both functions (often referred to as an "artificial pancreas") could theoretically maintain near normal blood glucose levels.

Continuous subcutaneous insulin infusion (CSII) via pumps provides a closer approximation of normal plasma insulin profiles and increased flexibility regarding timing of meals and snacks compared to conventional insulin injection regimens.

In addition, insulin pump therapy in Diabetes Mellitus is associated with improved metabolic control and reduced risk of severe hypoglycemia compared to multiple daily injections of insulin.

Several ambulatory insulin infusion devices are currently available on the market. First generation pumps fitted with disposable syringe-type reservoirs and tubes are described by in U.S. Pat. No. 3,631,847 to Hobbs, U.S. Pat. No. 3,771,694 to Kaminski, U.S. Pat. No. 4,657,486 to Julius, and U.S. Pat. No. 4,544,369 to Skakoon. The main drawbacks of these devices are their large size and the weight, caused by the spatial configuration and the relatively large driving mechanism of the syringe and the piston. The relatively bulky device is carried in a patient's pocket or attached to the belt or some other article of clothing. Consequently, the fluid delivery tube is typically quite long, usually longer than 60 cm, to permit needle insertion in remote sites of the body. These uncomfortable, bulky devices with a long tube are rejected by the majority of diabetic insulin users, because they tend to disturb regular activities, such as for example sleeping and swimming. Furthermore, the effect of the image projected on a teenagers' body is unacceptable. In addition, the presence of the delivery tube excludes some otherwise potentially preferable remote insertion sites, like the buttocks and the extremities.

Pumps can be provided with a housing having a bottom surface adapted for contact with the patient's skin, a reservoir disposed within the housing, and an injection needle adapted for communication with the reservoir. These skin adhered pumps should be disposed of every 2-3 days like current pump infusion sets. This paradigm was described by Burton in U.S. Pat. No. 5,957,895, Connelly, in U.S. Pat. No. 6,589, 229, and by Flaherty in U.S. Pat. No. 6,740,059. Other configuration of the skin adhered pumps are disclosed in U.S. Pat. Nos. 6,723,072 and 6,485,461. The pump can include a single piece that adheres to the patient skin for the entire usage duration. The needle emerges from the bottom surface of the pump and is fixed to the device housing. These so-called "second-generation" skin adhered devices tend to be expensive, bulky and heavy.

Current diabetic patients generally measure their own blood glucose level discontinuously, on the order of perhaps several times during the day. Blood glucose sampling typically includes obtaining finger-prick capillary samples and applying the blood to a reagent strip for analysis done in a portable meter. The discomfort involved with these methods often leads to poor patient compliance. Testing cannot be performed while sleeping and while the subject is occupied. In addition, the results do not give information regarding trends in glucose levels, but rather provide only discrete readings, taken at typically large time intervals between consecutive measurements. Therefore it would be desirable to carry out the glucose monitoring substantially continuously by performing discrete measurements, at a very high rate. Continuous monitoring can be done by invasive, minimally-invasive, or non-invasive means.

Minimally-invasive glucose monitors can measure glucose levels in the interstitial fluid (ISF) present within the subcutaneous tissue. The strong correlation between blood and ISF glucose levels has been shown to facilitate accurate glucose measurements (*Diabetologia* 1992; 35, (12): 1177-1180).

The GlucoWatch G2® Biographer (available from Cygnus, Inc., Redwood City, Calif.) is one commercially available minimally-invasive glucose monitor whose function is detailed in U.S. Pat. No. 6,391,432. A small current passing between two skin-surface electrodes draws ions and (by electro-endosmosis) glucose-containing interstitial fluid to the skin-surface and into hydrogel pads provided with a glucose oxidase (GOX) biosensor (*JAMA* 1999; 282: 1839-1844). Readings are taken every 10 min, with a single capillary blood calibration. Disadvantages of the GlucoWatch® are associated with occasional sensor values differing markedly from blood values; with skin rashes and irritation in those locations which are immediately underneath the device, appearing in many users; with a long warm up time of 3 hours; and with skips in measurements due to sweating.

Another commercially available minimally-invasive monitor is the Guardian® RT Continuous Glucose Monitoring System (available from Medtronic MiniMed Inc., Northridge, Calif.). This device is a GOX-based sensor, which is described in U.S. Pat. No. 6,892,085. The sensor consists of a subcutaneously implanted, needle-type, amperometric enzyme electrode, coupled with a portable logger (*Diab. Tech. Ther.* 2000; 2: Supp. 1, 13-18). The Guardian® RT system displays updated glucose readings every five minutes, together with hypo- and hyperglycemic alarms. The sensor is based on the technology of GOX immobilized at a positively charged base electrode, with electrochemical detection of hydrogen peroxide production. This enzymatic reaction, when carried out in-vivo, can encounter stoichiometric hurdles that can compromise its accuracy. The device is large and bulky and requires inconvenient tubing.

Closed loop infusion systems, such as the system described in U.S. Pat. No. 6,558,351, can include a sensor system and a delivery system. The systems can be coupled via a controller that uses the inputs of the sensor system to generate commands to the delivery system. The main shortcoming of the described closed loop system is that two separate devices, comprising separate tubing and separate cannulae should be applied to the body of the user.

Measurement of the glucose concentration in a sample can be performed using one or more methods. The most common methods today are electrochemical measurement techniques and optical measurement techniques. The detection principle of enzyme-based sensors is based on monitoring of the enzyme-catalyzed oxidation of glucose. These include glucose sensors using amperometric or potentiometric operating principles.

The enzymatic reaction that occurs in the majority of these sensors is catalyzed by glucose oxidase (GOX). In this reaction, oxygen and glucose yield gluconic acid and hydrogen peroxide. In this reaction, in which glucose is oxidized to gluconic acid, glucose oxidase acts temporarily as an electron acceptor, which means that it is first reduced to an inactive state and is subsequently reactivated by the reduction of oxygen to hydrogen peroxide. The analyte concentration is transduced into a detectable signal, generally by using amperometric methods.

Ex vivo amperometric glucose sensors are often mediator-based. A mediator-based glucose sensor uses an artificial electron acceptor, or mediator, to replace the natural acceptor, oxygen, in the oxidation of glucose by GOX and thus is not oxygen dependent. The oxidation of the reduced mediator occurs at a low potential, thus reducing the sensitivity of the sensor to interfering substances.

Many in vivo devices are mediatorless due to possible leaching and toxicity of the mediator. Illustrative examples of mediatorless devices are described in U.S. Publication No. 2005/0272989 assigned to MiniMed, and U.S. Pat. No. 6,975,893 assigned to Abbott. These devices generally rely on oxygen as a physiological electron acceptor. Arterial blood has a glucose-to-oxygen ratio of approximately 10 to 1, while venous blood has a glucose-to-oxygen ratio of about 100 to 1. Thus, in vivo devices often use membranes to tailor the flux of glucose and oxygen to the enzymatic coating on the electrode. Different layers alter the diffusion of one or more analytes into the area that comprises the catalytic enzyme or enzymes. The stoichiometric scarcity of oxygen in vivo can present an obstacle to the effectiveness of these devices. In addition, these devices are subjected to errors due to fluctuations in the concentration of dissolved oxygen.

Amperometric measurement of hydrogen peroxide requires application of a potential at which additional electroactive species, such as for example ascorbic and uric acids or acetaminophen are present. These and other oxidizable constituents of biological fluids can compromise the selectivity and hence the overall accuracy of the glucose concentration measurement. Hydrogen peroxide can have toxic effects that may compromise the biocompatibility of the sensor. This poses a problem mainly when the hydrogen peroxide is not consumed for the transduction (that is, when the biosensor is not based on hydrogen peroxide). Application of catalase may resolve this setback. Hydrogen peroxide also tends to deactivate the GOX molecules, limiting the time available for application of the sensor. Overloading the sensor with an excess of enzyme, more than what is required to catalyze the incoming glucose, may be helpful in overcoming this problem. Co-immobilization of catalase may be beneficial. However, this solution is more appropriate for glucose sensors based on the detection of $O_2$ that do not depend on measuring $H_2O_2$. Furthermore, catalase is in turn inactivated by hydrogen peroxide (*Diab. Tech. & Ther*. Vol. 2, No. 3, 2000, pp. 367-376). Additionally, the size of such probes, including the sensing unit with its various layers, is relatively large, affecting the ease and comfort of the probe insertion into the user's body. Miniaturizing the sensing technology within the probe, which requires high levels of enzyme loading, while keeping high measurement sensitivity, remains a challenge.

Microdialysis is an additional commercially available minimally-invasive technology (*Diab. Care* 2002; 25: 347-352) for glucose monitoring as detailed in U.S. Pat. No. 6,091,976 to Pfeiffer (assigned to Roche Diagnostics, Basel, Switzerland) and used in the GlucoDay® S (available from Menarini Diagnostics, Florence, Italy). A fine, semi-permeable hollow dialysis fiber is implanted in the subcutaneous tissue and perfused with isotonic fluid. Glucose diffuses across the semi-permeable fiber and is pumped outside the body via the microdialysis mechanism for measurement by a glucose oxidase-based electrochemical sensor. Initial reports (*Diab. Care* 2002; 25: 347-352) show good agreement between sensor and blood glucose readings, and good stability with a one-point calibration over one day. Higher accuracies were found when using the microdialysis-based sensor, compared to the needle-type sensor (*Diab. Care* 2005; 28, (12): 2871-6).

Disadvantages of the microdialysis-based glucose sensors stem primarily from the constant perfusion of solution through the microdialysis probe. This operational method requires the presence of a dedicated pump and reservoir, leading to large and bulky devices, and also necessitates high energy consumption. Furthermore, the relatively large size of the microdialysis catheter often causes a wound and subsequent local tissue reactions following its insertion into the subcutaneous tissue. Finally, the microdialysis process generates long measurement lag times, due to the essential slow perfusion rates and long tubing.

Optical glucose measurement techniques can be attractive for several reasons: they utilize non-ionizing electromagnetic radiation to interrogate the sample, they do not generally require consumable reagents, and they are fast. Also, these techniques are generally non-destructive and reagentless, thereby reducing the risk of unsafe reactions and their byproducts. Although optical approaches for glucose sensing are attractive, they can nevertheless be plagued by a lack of sensitivity and/or specificity since variations in optical measurements depend on variations of many factors in addition to glucose concentration. Isolating those changes which are due to glucose alone and using them to predict glucose concentration is a significant challenge in itself (*J. Biomedical Optics* 5 (1), 5-16 Jan. 2000). Furthermore, non-invasive optical glucose monitors, which involve sensing of glucose concentration levels through the skin, involve very low signal-to-noise ratio, scattering and interferences by bodily fluids and by the skin itself, causing non-invasive optical sensors to lack specificity and repeatability.

SUMMARY

In one aspect, an apparatus includes a patch unit having a skin contact surface, a cannula having an insertable end that protrudes from the skin contact surface for insertion into a subcutaneous compartment of a user, a detector system, a reversible pumping mechanism for displacing fluid through the cannula, and a control processor that controls the pumping mechanism such that the reversible pumping mechanism is configured to draw a volume of analyte-enriched fluid from the subcutaneous compartment into a sampling space and then to reverse the volume of fluid to the subcutaneous compartment after the detector system quantifies a concentration of at least one analyte in the sampling space.

In an interrelated aspect, a method includes withdrawing a volume of an analyte-enriched fluid out of a subcutaneous compartment of a user of a patch unit. The withdrawing occurs under the influence of a pumping mechanism in the patch unit. The pumping mechanism operates to displace the volume in a reverse direction such that the volume is withdrawn out of the subcutaneous compartment and into the patch unit through a cannula inserted within the subcutaneous compartment. An analyte concentration in the volume can be measured using a sensing element within the patch unit. At least the volume is delivered back into the subcutaneous compartment by operating the pumping mechanism to displace at least the volume in a forward direction.

In some variations one or more of the following features can optionally be included. A biologically compatible fluid can optionally be pumped from a reservoir in the patch unit that is in fluid communication with the cannula into a part of the cannula that is insertable within the subcutaneous compartment by operating the reversible pumping mechanism to displace the fluid in a forward direction. Fluid delivery can optionally be suspended by setting the pumping mechanism in a static state such that the biologically compatible fluid achieves a partial or complete analyte concentration equilibrium with interstitial fluids in the subcutaneous compartment. The partial or complete analyte concentration equilibrium can optionally occur by transport of molecules of an analyte from the interstitial fluids to the biologically compatible fluid such that the biologically compatible fluid becomes the analyte-enriched fluid. The reversible pumping mechanism can optionally be configured to displace the biologically compatible fluid from the reservoir into the subcutaneous compartment via the cannula, which can optionally include a dispensing arm and a sensing arm such that the dispensing arm delivers the biologically compatible fluid from the reservoir into the subcutaneous compartment and the sensing arm withdraws analyte-enriched fluid from the subcutaneous compartment to the detector system for quantifying the concentration of the at least one analyte. A regulation means can optionally be included to prevent analyte-enriched fluid from entering the reservoir. The reversible pumping mechanism can optionally include a peristaltic mechanism or a syringe and plunger mechanism. The patch unit can optionally further include a power source.

The insertable end of the cannula can optionally include a surface that is permeable or semi-permeable such that the at least one analyte diffuses across the surface from interstitial fluid within the subcutaneous compartment to biologically compatible fluid within the cannula to create the analyte-enriched fluid. Alternatively, the insertable end can optionally include a surface that is permeable or semi-permeable such that the at least one analyte microperfuses across the surface from interstitial fluid within the subcutaneous compartment to biologically compatible fluid within the cannula to create the analyte-enriched fluid.

The patch unit can optionally further include a disposable part that includes the reservoir and a reusable part that includes the control processor, at least part of the detector system, and at least part of the pumping mechanism. The patch unit can be operable upon connection of the disposable part and reusable part. A cradle unit can further optionally be included such that the cradle unit includes the skin contact surface. The cradle unit can be configured to mate with the patch unit. The patch unit can optionally be connectable to and disconnectable from the cradle unit. One or more components of the detector system can optionally reside in each of the reusable part and the disposable part. A disposable cannula cartridge unit that includes the cannula can also optionally be included. The disposable cannula cartridge unit can mate with the cradle unit to position the insertable end relative to the skin contact surface and provide a fluid-tight seal for interfacing with the reservoir The control processor can optionally initiate a change to a delivery rate of the biologically compatible fluid based on the quantified concentration of the at least one analyte. The control processor can optionally promote a notification to a user interface. The notification can optionally request authorization of a proposed change to a delivery rate of the biologically compatible fluid based on the measured analyte concentration. A remote control device that includes means for receiving fluid delivery programming commands can optionally be included. The remote control unit can communicate with the patch unit and provide the user interface. One or more buttons can optionally be provided on the patch unit that permit entry of fluid delivery programming commands.

The analyte concentration can optionally be measured via electrochemical or optical sensing. The biologically compatible fluid can optionally be insulin or saline, and the analyte can optionally be glucose.

Articles are also described that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed embodiments. In the drawings.

FIG. 29 is a schematic diagram showing a fluid reciprocating system fitted with a double lumen cannula;

FIG. 30 is a schematic drawing showing another double lumen cannula;

DETAILED DESCRIPTION

Figure 1:
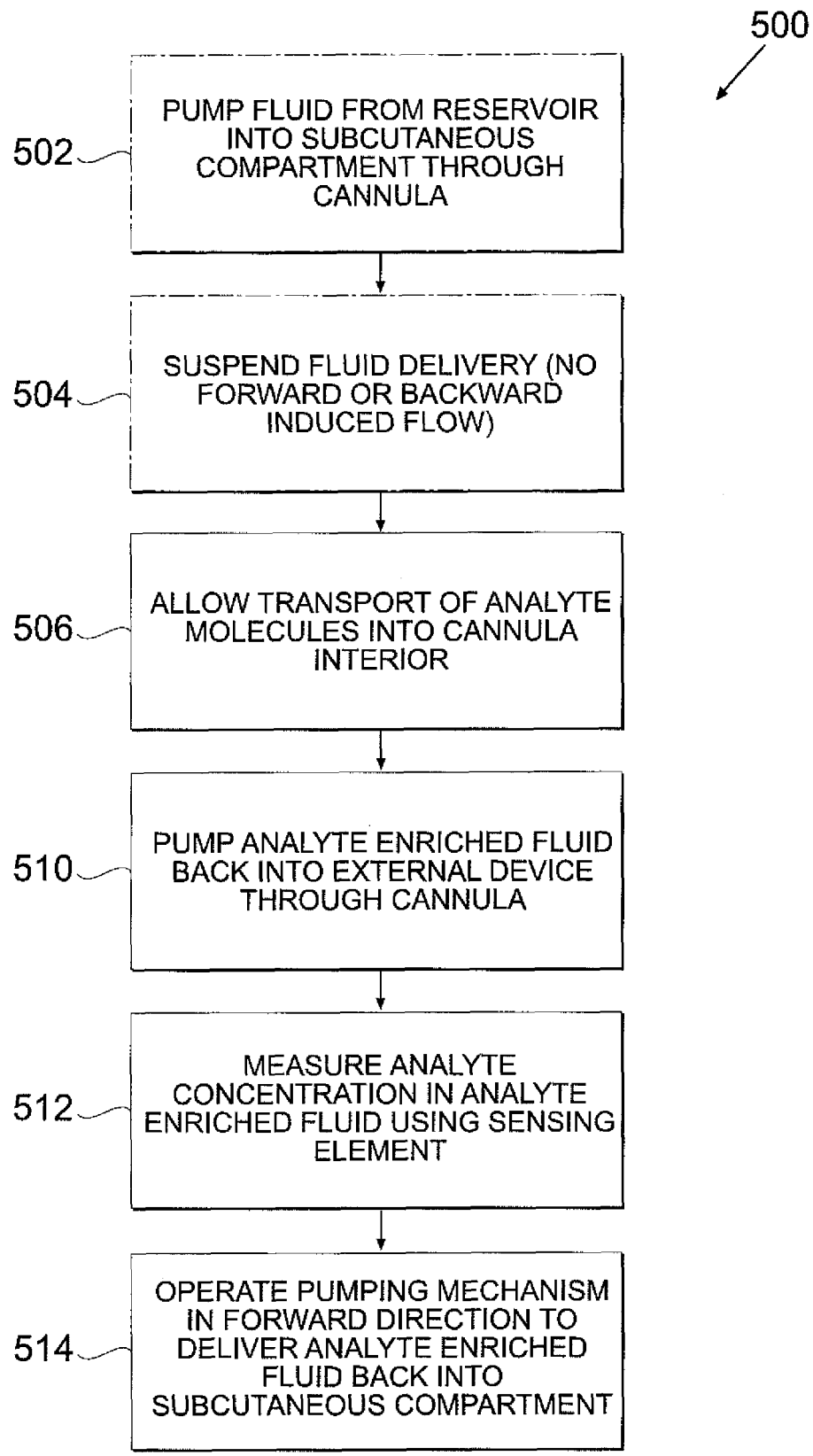
FIG. 1 is a process flow chart showing a method for analyte sensing and fluid delivery.

The current subject matter provides, among other possible features and benefits, systems, methods, techniques, articles of manufacture, and apparatuses that enable extracorporeal monitoring of one or more analytes in a subject's body. Analyte levels can also be monitored by extracorporeal means that concomitantly deliver fluids into the body. Such a system will henceforth be referred to as a "dispensing and monitoring patch unit" or a "patch unit." Such dispensing and monitoring patch units can be miniature, single-piece or two-piece devices that are discreet, economical for the users and highly cost effective for the payer. Fluid delivery programming and data acquisition can be carried out in some implementations by a separate, remote control unit and/or by manual buttons or some other form of user interface located on the patch itself. A remote control unit can be one or more of a dedicated wireless or wired unit the communicates with the patch unit, or alternatively a cell phone or personal data assistant, a computer, an MP3 player, or the like.

Miniature portable programmable dispensing and monitoring patch units as disclosed herein can be made without long external tubing and can be attached to the patient at any desired location on the body. The current subject matter further encompasses relatively simple and inexpensive dispensing and monitoring patch units that are composed of disposable and reusable parts. After connecting the reusable and disposable parts, such a whole device can have a thin profile and a relatively small footprint that renders it quite discreet. A disposable part can be composed of few parts, will be easy to manufacture and assembly, and will be cheap. The sealing between the parts after they are connected can be complete or nearly complete therefore have little or no negative effect on the device's function. Dispensing and monitoring patch units can be capable of being disconnected from and reconnected to a subject's body in a safe, reliable and user-friendly manner. Disconnections and reconnections would desirably neither harm the dispensing and monitoring patch unit components nor the surrounding body tissues. Devices in accordance with the current subject matter can continuously monitor glucose levels and continuously or nearly continuously dispense insulin or can alternatively be configured to continuously or nearly continuously dispense one or more other fluids and to monitor the levels) of one or more analytes. Closed loop systems that monitor glucose concentration levels and dispense insulin according to said sensed glucose levels are within the scope of this subject matter, as are devices that monitor analyte levels and concomitantly deliver fluids, for example via a single subcutaneous cannula suitable for analyte monitoring and for fluid dispensing. In other implementations, a device having two subcutaneous cannulae can monitor analyte levels and concomitantly deliver fluids. One cannula can be dedicated to analyte monitoring and the second cannula can be dedicated to fluid dispensing.

Various devices according to the current subject matter can extra-corporeally monitor subcutaneous interstitial fluid (ISF) analyte levels, such as for example glucose, and concomitantly dispense fluids, such as for example insulin. Subcutaneous ISF analyte levels can be measured extra-corporeally for a fluid that is transported outside of the body. Monitor for glucose and/or one or more other analytes can be based on electrochemical or optical measurement means placeable above the skin. Insulin and/or some other therapeutic, medicinal, or other fluid can be delivered into the body while levels of glucose and/or some other analyte can be measured using electrochemical or optical measurement means that are placeable above the skin. Fluid, either originating in the body or injected or infused from outside the body can be withdrawn to outside the body for monitoring analyte levels. This withdrawn fluid can be delivered back into the body after the analyte level has been determined.

In general, for balanced management of diabetes, continuous or semi-continuous glucose monitoring alone is generally not sufficient. Tighter glycemic control can be achieved by substituting both functions of the normal pancreas: glucose sensing and insulin delivery. A closed loop system provided with a feedback mechanism could theoretically maintain near normal blood glucose levels. Such a closed loop system, referred to as an "artificial pancreas", would include an insulin pump and a continuous glucose sensor that work together to imitate the human pancreas. The continuous glucose sensor would report the measured glucose values to the insulin pump, which then supplies the appropriate dose of insulin and delivers it to the user's body. In a semi-closed loop system, user inputs can be added as supplementary inputs to the system, in addition to the continuously measured glucose values measured by the sensor, and both inputs can be used for determining appropriate insulin dosage.

Currently available artificial pancreatic systems can contain a sensor and pump which are two discrete, expensive components, each confined in a separate housing, where both relatively bulky and heavy devices should be attached to the user's belt or skin. In addition, the pump generally requires an infusion set with long tubing and the two devices require two insertion sites, consequently extending the system's insertion and disconnection times, increasing pain caused by skin pricking and substantially increasing adverse events like infections, irritations, bleeding, etc.

In one implementation, a device can include a dispensing apparatus and a sensing apparatus. The dispensing apparatus infuses fluid into the body of a user. The sensing apparatus detects the concentration level of at least one analyte present within the user's body and monitors this concentration level. The device can optionally be composed of a skin adherable patch unit that includes, among other components, a dispensing apparatus, a sensing apparatus, a fluid reservoir, a pumping mechanism, a cannula, and electronic parts. The reservoir contains fluid to be dispensed into the body, such as isotonic fluid or therapeutic fluid (e.g. insulin). The flow of fluid from the reservoir is controlled by a pumping mechanism. Fluid flows into the body of a user via a cannula, which is inserted into the subcutaneous compartment in the body.

The monitored analyte in some implementations can be glucose and the dispensed fluid can be insulin, to be used with diabetic patients. Alternatively, the monitored analyte can be glucose and the dispensed fluid is saline, or another biologically compatible or physiological fluid. The sensing of analyte concentration levels and the dispensing of one or more fluids can in some implementations both be carried out with a single cannula. The sensing apparatus and dispensing apparatus can share a common cannula, a common fluid reservoir, and a common pumping mechanism. In this configuration, the device contains a single cannula, a single fluid reservoir and a single pumping mechanism.

The dispensing apparatus and the sensing apparatus can work in a closed loop system in some implementations in which a processor-controller apparatus regulates the dispensing of a fluid according to the sensed analyte concentration. Alternatively, the dispensing apparatus and the sensing apparatus can operate in a semi-closed loop system in which a processor-controller apparatus regulates the dispensing of the fluid according to the sensed analyte concentration and/or according to external user inputs. The dispensing and sensing apparatus can also operate in an open loop system in which the sensing and the delivering functions are not coupled into a feedback loop but can operate fully independently of one another.

In some implementations, the device can include a reusable part and a disposable part. The reusable part can optionally contain relatively expensive components of the system, including electronic elements, driving elements, and some of the sensing elements. The disposable part can optionally contain non-reusable and less expensive parts of the system, including one or more of a fluid reservoir, a cannula, and disposable elements of the sensing means.

The cannula walls can be configured as a permeable or semi-permeable membrane enabling diffusion or perfusion of analyte molecules, such as for example glucose) into the cannula. This intra cannula space can be occupied either by an isotonic dispensed fluid, or by a therapeutic fluid, such as for example insulin. The diffusion or perfusion process that occurs across the permeable or semi-permeable membrane, allows analyte molecules, such as for example glucose, to follow the concentration gradient and rapidly achieve partial or full equilibrium (sometimes referred to as full or partial "recovery"). The analyte concentration in the fluid within the cannula is generally proportional or equal to the analyte concentration in the interstitial fluid (ISF) surrounding at least a portion of the cannula. Thus, quantification of the analyte concentration in the fluid extracted from the cannula can be used to determine the analyte concentration in the ISF or other fluid in the subcutaneous compartment. The pumping mechanism, which is also referred to as a reversible pumping mechanism or a reciprocating pumping mechanism, can optionally be a peristaltic-type pump, a mechanism having a plunger that drives fluid to be dispensed out of a syringe-type reservoir, a piezoelectric mechanism, or any other configuration that allows fluid to be moved in a forward and reverse direction.

The fluid dispensing and analyte sensing can be synchronized in a continuous cycle as described below and shown in the process flow chart 500 of FIG. 1. Forward pumping of a pumping mechanism in a patch unit can optionally deliver fluid from the reservoir into the subcutaneous compartment through the cannula in a fluid delivery phase at 502. Pumping and fluid delivery can optionally be suspended such that no forward or backward fluid motion occurs at 504. Endogenous molecules of analyte (such as for example glucose) from the interstitial fluid (ISF) in the subcutaneous compartment are allowed to transport (for example by diffusing, perfusing or permeating) across the cannula walls (which is either semi or fully permeable) into the cannula interior at 506, while the concentration of the endogenous molecules in the fluid within the cannula's interior reach partial or full equilibrium in a diffusion or perfusion phase. It is also possible to perform analyte sensing according to the current subject matter using an impermeable cannula. In such a system, fluid from the subcutaneous compartment could, for example, be drawn up through the cannula. Analyte-enriched fluid is pumped backwards by action of the pumping mechanism into or into proximity with a sensing element located within the patch unit, above the skin at 510 in a fluid withdrawal phase. Analyte concentration levels in the analyte enriched fluid are sensed by the sensing and control elements at 514 in a sensing phase. The pumping mechanism is again operated in the forward direction to deliver the fluid back into the subcutaneous compartment at 514

FIG. 2 provides several schematic diagrams that illustrate devices that are consistent with the disclosed subject matter. In general, a device is composed of a patch unit 1010 that may adhere to the user's skin 5. A remote control unit 1008 can be provided to present a user interface via which a user, technician, physician, or the like can communicate with the patch unit 1010 to among other possible uses, input commands or other data and/or receive reports of measured concentrations, alerts and/or action recommendations. A sensing element 2000 is located in the patch unit 1010, and therefore above the surface of the skin 5. At least one subcutaneous cannula 6 is provided for delivering fluid from a reservoir (not shown) located in the patch unit 1010 to the body and/or to transfer fluid from the body to the sensing element 2000. Operation of the patch unit 1010 can be performed optionally either via the remote control unit 1008 or by one or more buttons 15 or other user interface features that are on the patch unit 1010.

Figure 2A:
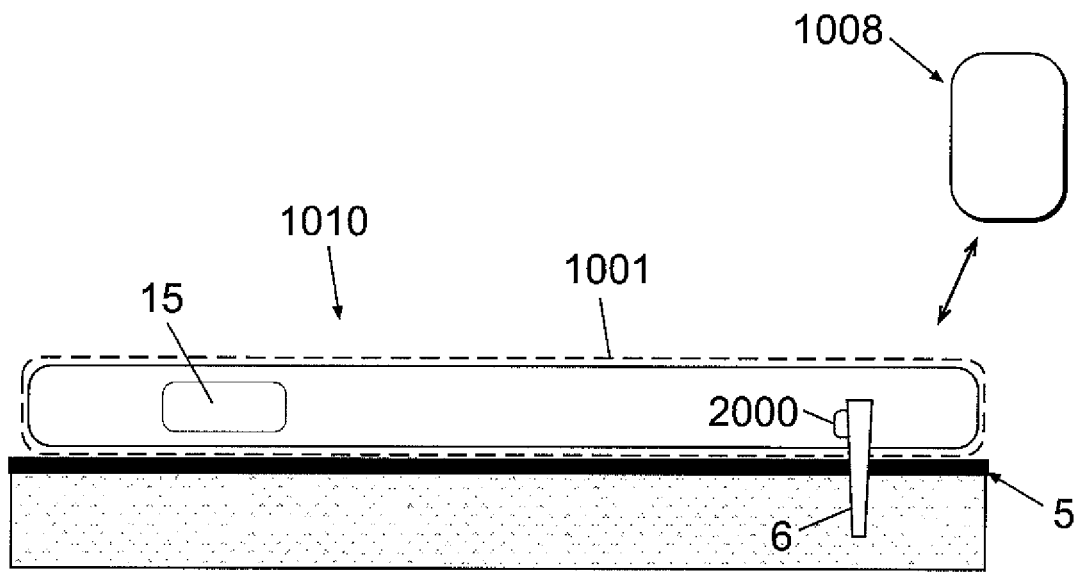
FIG. 2 are schematic diagrams showing a general configurations of devices that include a patch unit and a remote control unit, with (a) a single-part patch unit confined in a single housing, (b) a two-part patch unit confined in two separate respective housings, and (c) a patch unit that includes a cradle that contacts the skin and that mates with one or more additional parts to form the patch unit.
Figure 2B:
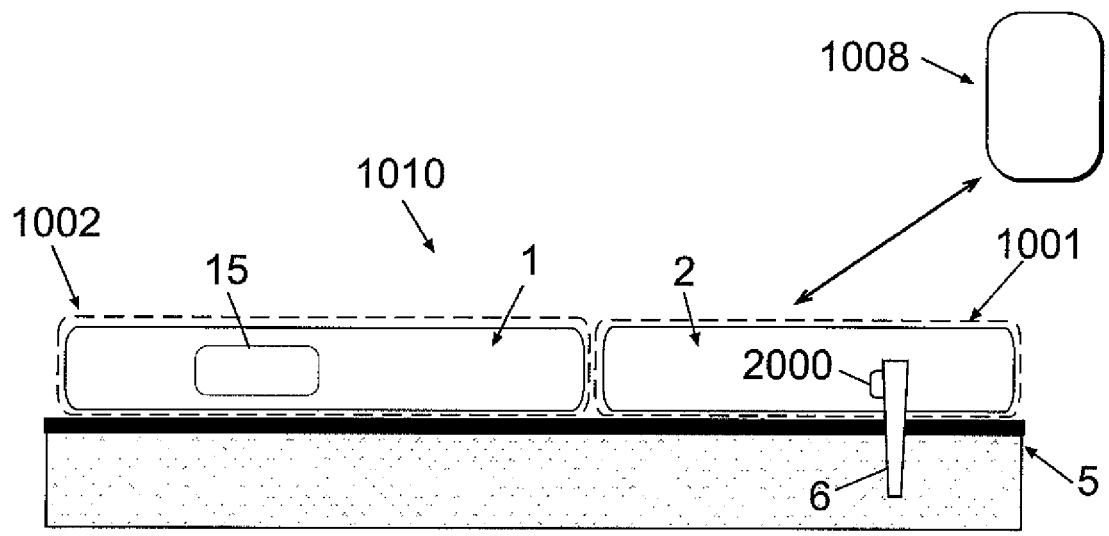
Figure 2C:
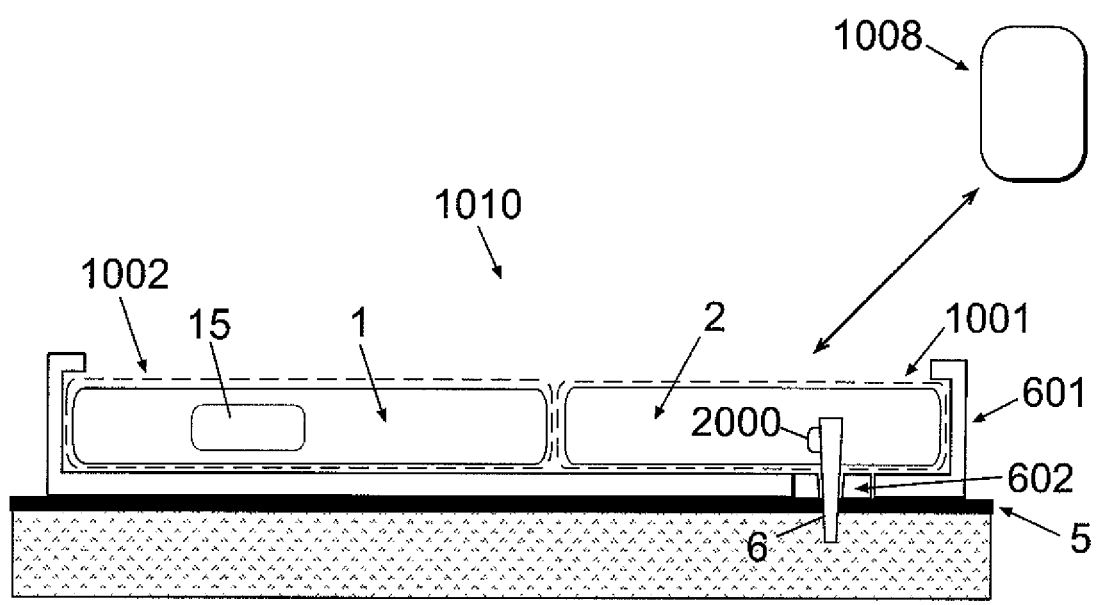

The patch unit 1010 can be configured as a single part having one housing 1001, as shown in FIG. 2a, or can include two parts having two separate, connectable housings 1, 2 as shown in FIG. 2b. FIG. 2c shows a third optional configuration for patch unit that includes a cradle 601 that provides contact with the skin 6 of the user. Two additional parts having separate housing 1, 2 nest into the cradle 601. The cannula 6 can optionally be provided in a detachable cannula cartridge unit 602 that mates with the cradle 601. The cannula cartridge unit can include the cannula and a fluid-tight connection that can interface with tubing, the pumping mechanism, or the reservoir when the disposable and reusable parts 1, 2 are connected. In one example, the end of the cannula opposite the end that is adapted to be inserted into the subcutaneous compartment can have a septum that interfaces with a needle or mating cannula of some other part of the fluid movement and delivery system of the patch unit.

Other configurations of the device that perform the functions described herein and claimed below are also within the scope of the current subject matter. The patch unit 1010, which can also be referred to as a cradle unit in some implementations, can be attached directly to the skin surface 5, or via a needle unit (not shown) such as is disclosed in U.S. Provisional Application for Patent No. 60/876,679 or by using a well as disclosed in U.S. Provisional Application for Patent Nos. 60/833,110 and 60/837,877. The cradle unit enables the connection/reconnection and disconnection the patch unit to and from the body. While the patch unit is connected to the body, fluid communication between the reservoir (located in the patch unit) and the cannula inserted in the body is maintained.

Figure 3:
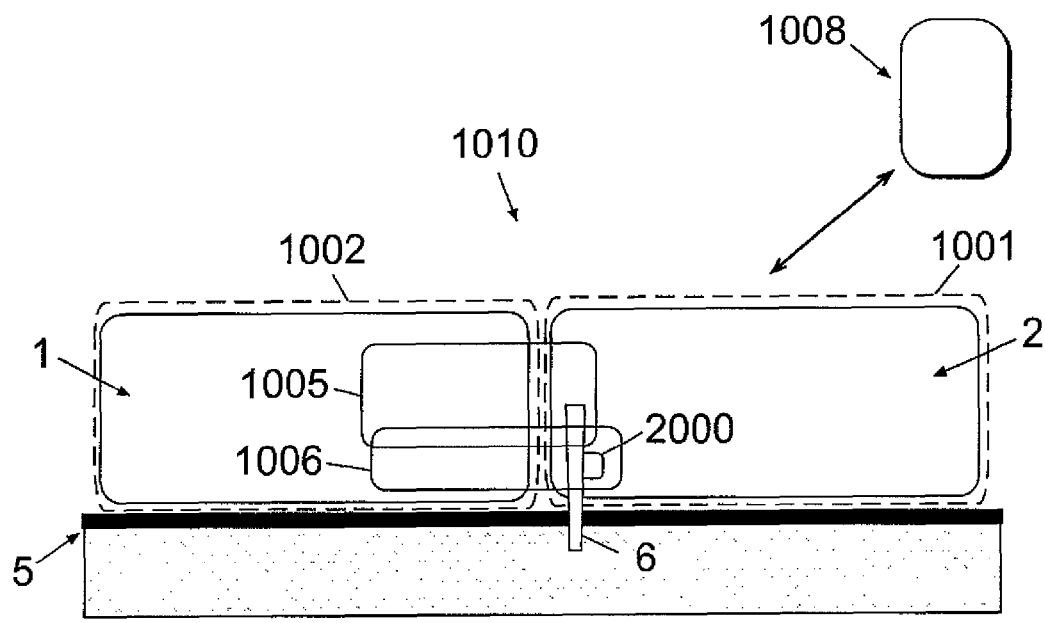
FIG. 3 is a schematic diagram of a two-part patch unit, including the dispensing and sensing apparatuses.

FIG. 3 is a diagram showing an implementation of the device in which the patch unit 1010 includes a reusable part 1 and a disposable part 2. Each part can be deployed in its own housing 1002, 1001, respectively. The device can also include a sensing apparatus 1006 and a dispensing apparatus 1005. The various components of each apparatus can reside partly in the reusable part 1 and partly in the disposable part 2. Relatively cheap components, such as for example the cannula 6, reservoir, and disposable components of the sensing element 2000 can reside in the disposable part 2. Relatively more expensive components, such as for example electronic processing elements and/or an occlusion sensor, and the like can reside in the reusable part 1. Certain components of the sensing element 2000 can also be located in the reusable part 1. As noted above, the dispensing apparatus 1005 and sensing apparatus 1006 can use a single cannula to perform dispensing and sensing operations and can in some implementations operate as a closed-loop system.

Figure 4:
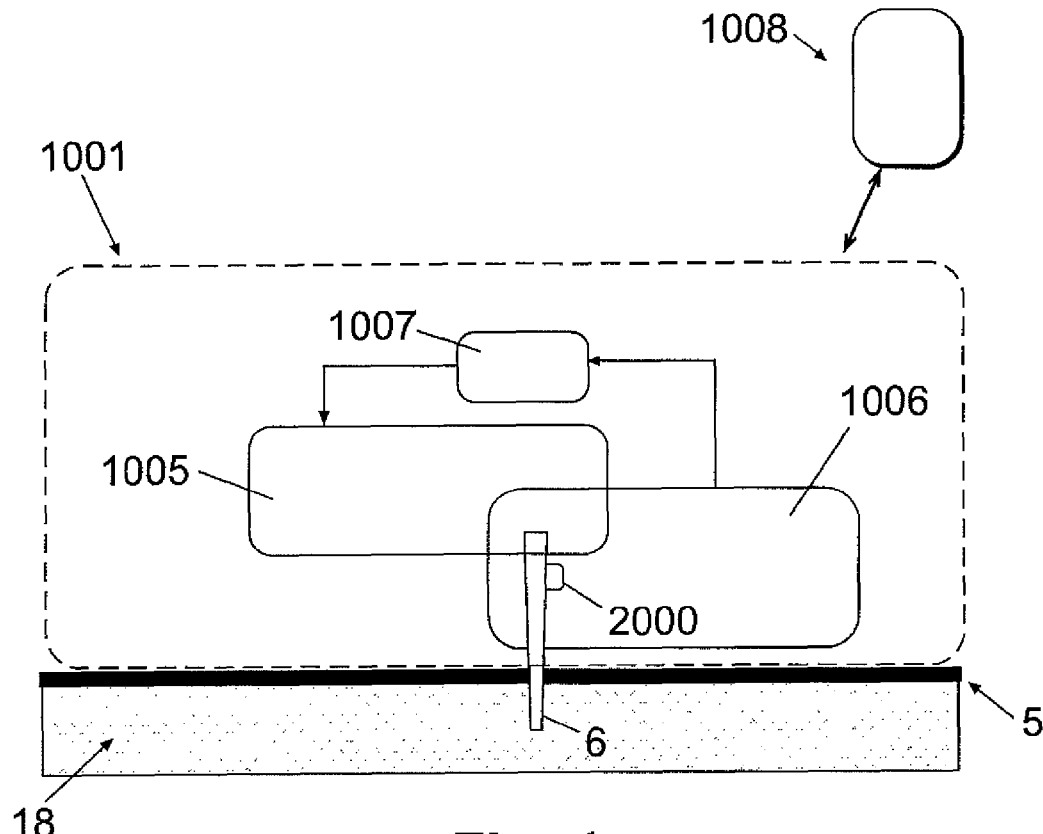
FIG. 4 is a schematic diagram of a device in which the dispensing apparatus and sensing apparatus use a common, single cannula and operate as a closed-loop system.

FIG. 4 shows another implementation of a device in which the dispensing apparatus 1005 and sensing apparatus 1006 are accommodated in one housing 1001, and use a common single, dual function, cannula 6 inserted under the skin 5 within the subcutaneous tissue compartment 18 in the patient's body. A processor-controller apparatus 1007 can be provided within the housing 1001 for controlling the fluid dispensing (which can be saline, insulin, or some other biologically compatible or physiological fluid) according to a sensed concentration of one or more analytes, such as for example glucose, that is obtained by a sensing element 2000 provided in the sensing apparatus 1006.

In some implementations, bidirectional communication can be provided between the processor-controller apparatus 1007 and a remote control unit 1008. By virtue of this provision and/or by virtue of buttons or some other user interface feature on the housing 1001, data acquisition, programming, and user inputs (such as for example entry of data regarding meal carbohydrates consumed) can be accommodated. Functioning of such a device would be possible as a semi-closed loop system, or alternatively as a closed loop or open loop system. The device can be adhered to the user's skin 5 by adhesive means.

The dispensing apparatuses 1005 discussed herein can deliver fluid (e.g. saline, insulin) by other trans-cutaneous means (not shown) in addition to or instead of a subcutaneous cannula 6, for example by virtue of an array of miniature needles (micro-needle array), or by electrical, and/or ultrasound skin stimulations.

In various implementations, the patch unit can contain at least one reservoir and at least one pumping mechanism, which for example can be peristaltic, of a syringe and plunger type, or the like. The patch unit can in some implementations contain a single reservoir and a single pumping mechanism. In this configuration the reservoir is used for storing the fluid to be dispensed (e.g. saline, insulin, etc.). This fluid can also be used to assist in analyte (e.g. glucose) level sensing. The same reservoir could possibly be used also for receiving analyte (e.g. glucose) enriched fluid after sensing. The same pumping mechanism can be used for bidirectional fluid motion (reciprocating motion), for example from the reservoir to the body and from body towards the reservoir.

Figure 5A:
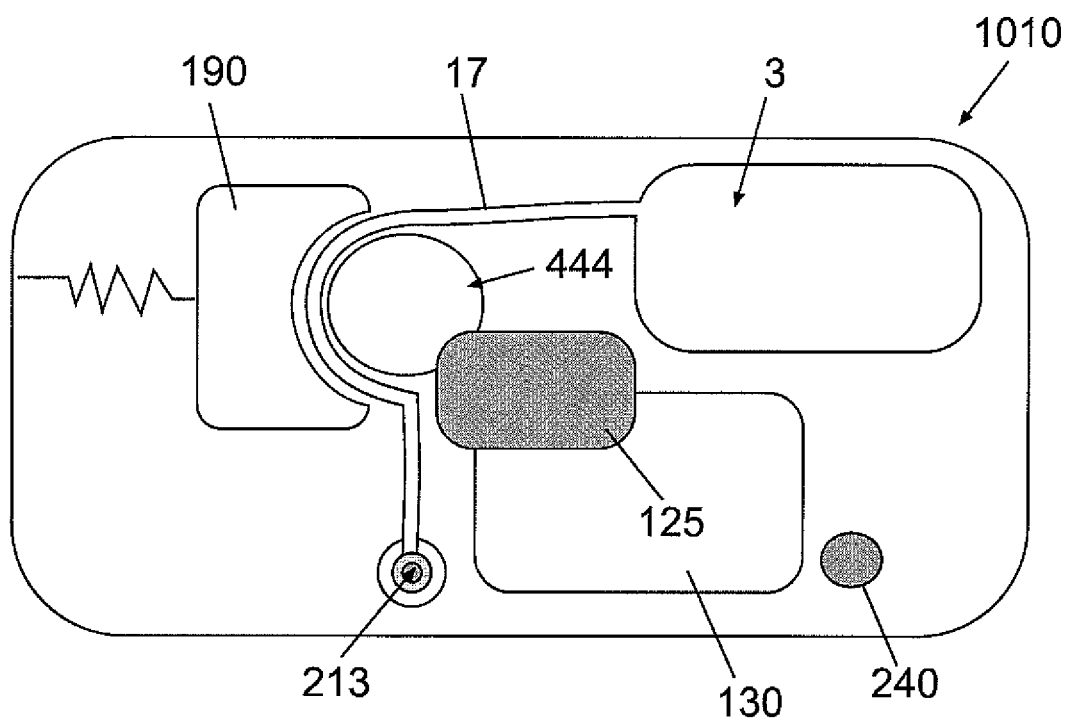
FIG. 5 are schematic diagrams of a device's interior including a peristaltic pumping mechanism associated with (a) a one-part patch unit or (b) a two part patch unit.

FIG. 5 shows two examples of patch units 1010 employing a peristaltic pump for dispensing the fluid to a user's body and for pumping the fluid backwards for monitoring concentration levels of body analytes. FIG. 5*a* shows a single-part patch unit 1010. The fluid is delivered from a reservoir 3 provided in the patch unit 1010 through a delivery tube 17 to the exit port 213. The peristaltic pump comprises a rotary wheel 444 that can be provided with rollers and a stator 190. Rotation of the wheel 444 and pressing of rollers against the stator 190 periodically positively displaces fluid within the delivery tube 17 by virtue of a peristaltic motion.

An example of such a positive displacement pump is disclosed in co-pending and co-owned Application for U.S. patent Ser. No. 11/397,115. A driving mechanism 125 that can include one or more gears and motors, such as for example a stepper motor, a DC motor, SMA actuator or the like, can be used for rotating the rotary wheel 444. The driving mechanism 125 can be controlled by electronic components residing in the patch unit 1010. Among such electronic components can be a controller, processor and transceiver. The electronic components are schematically designated by a common numeral 130 in FIG. 5*a* and FIG. 5*b*. Appropriate energy supply means 240 can also be provided, which can be one or more batteries or some other source of energy such as a solar cell, a fuel cell, an inductive power cell, or the like. Infusion programming can be carried out by a remote controller capable of establishing a bidirectional communication link with the transceiver provided in the patch unit 1010. Infusion programming can optionally or alternatively be carried out instead by manual buttons or other user interface features on the patch unit 1010.

Figure 5B:
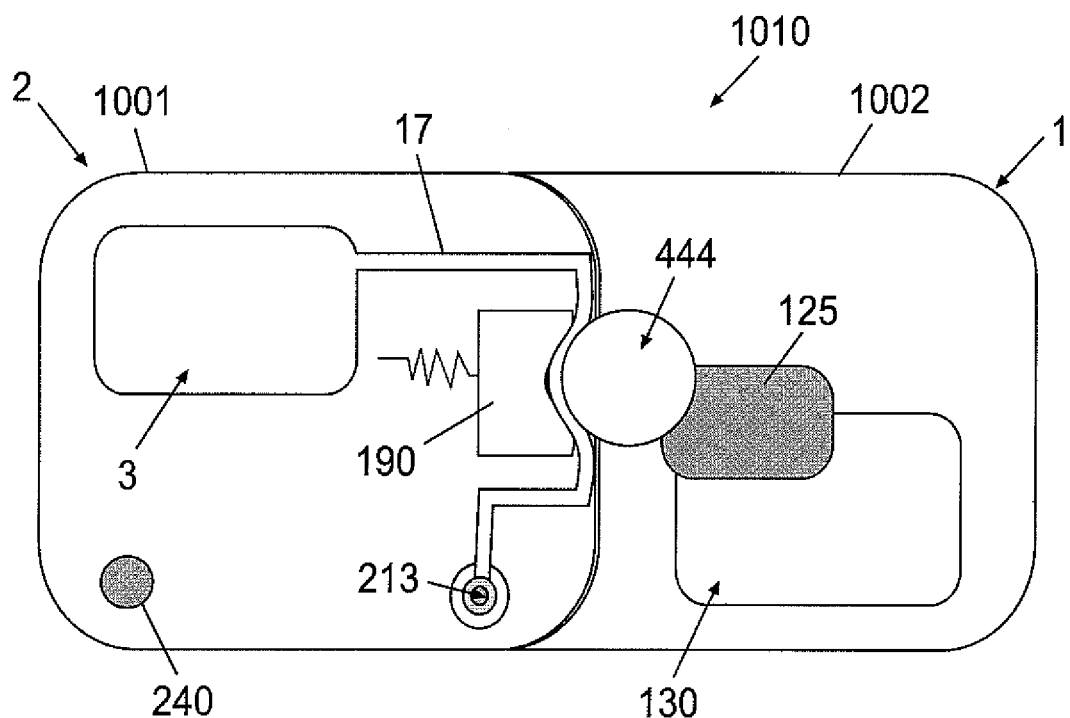

FIG. 5*b* shows a two-part patch unit 1010 that includes a reusable part 1 and a disposable part 2. The reusable part 1 includes a positive displacement pump provided with a rotary wheel 444, a driving mechanism 125 and electronic components 130 which can include those electronic components discussed above for FIG. 5*a*. The disposable part 2 includes a reservoir 3, a delivery tube 17, an energy supply means 240, an exit port 213 and a stator 190. Pumping can occur after connection of the reusable part 1 with the disposable part 2. This arrangement is described in co-pending and co-owned Application for U.S. patent Ser. No. 11/397,115. Other pumping mechanisms, for example syringe and plunger, piezoelectric, or the like can be used as well with minor variations to the above description.

Figure 6A:
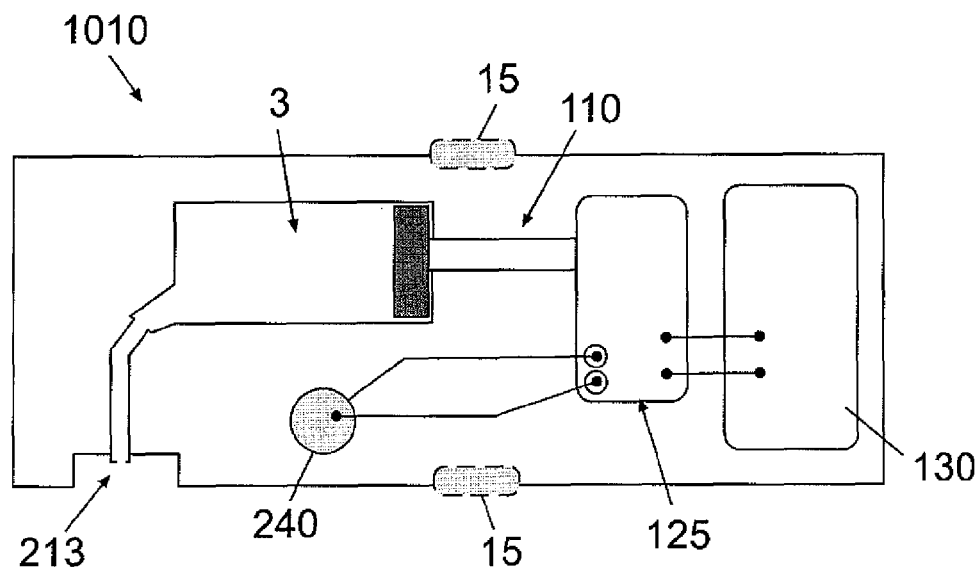
FIG. 6 are schematic diagrams of a device's interior including a piston pumping mechanism associated with (a) a one-part patch unit or (b) a two part patch unit.

FIG. 6 shows two examples of patch units 1010 employing a syringe pump for dispensing fluid to a user's body and for pumping fluid backwards for monitoring body analytes. FIG. 6*a* shows a single-part patch unit 1010. The fluid is delivered from a reservoir 3 to the exit port 213. The reservoir 3 is provided with a plunger 110 which urges the fluid towards the exit port 213. Driving mechanism 125 is provided, which can include a motor, such as for example a stepper motor, DC motor, SMA actuator or alike, and a driving gear for driving the plunger 110. The driving mechanism 125 is controlled by electronics 130.

Figure 6B:
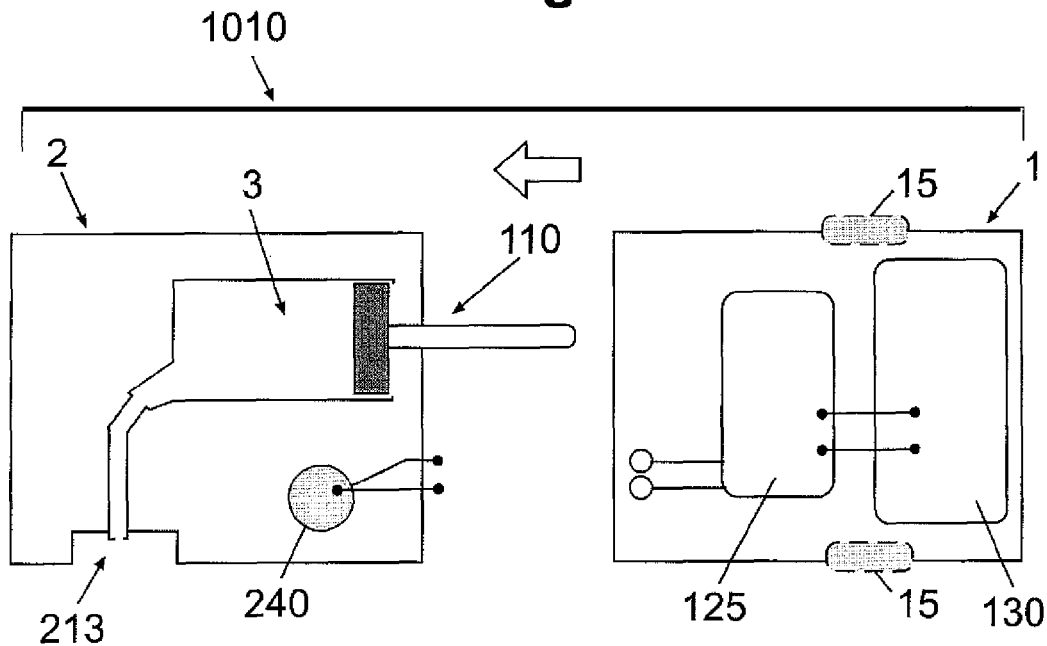

FIG. 6*b* shows a two-part patch unit 1010 comprising a reusable part 1 and a disposable part 2 employing a pumping mechanism 4, which is a positive displacement pump. The reusable part 1 comprises a driving mechanism 125 (for example motor and gears), electronic components 130, and at least one button 15. The disposable part 2 includes a reservoir 3 provided with a plunger 110, energy supply means 240, and exit port 213. In an alternative implementation, the plunger 110 can be located in the reusable part 1 or be shared by both parts. Infusion programming can be carried out by a remote controller and/or by one or more buttons 15 provided on the reusable part 1. Fluid dispensing is possible upon connecting the reusable part 1 with the disposable part 2.

FIG. 7 shows two examples of two-part patch units 1010. The patch unit 1010 is composed of a reusable part 1 and a disposable part 2. Each part is housed in a separate housing. The components of the dispensing apparatus and sensing apparatus are divided between the two parts of the patch unit 1010. The dispensing apparatus can include a reservoir 3, a delivery tube 17 and a cannula 6, all located within the disposable part 2. A pumping mechanism 4 can be located within the reusable part 1. In the dispensing apparatus, the pumping mechanism 4 delivers fluid from the reservoir 3 through the delivery tube 17 and cannula 6 into the user's body. The pumping mechanism 4 is also confined in the sensing apparatus. A processor-controller apparatus 1007 along with other electronic components of the device can be located in the reusable part 1.

Figure 7A:
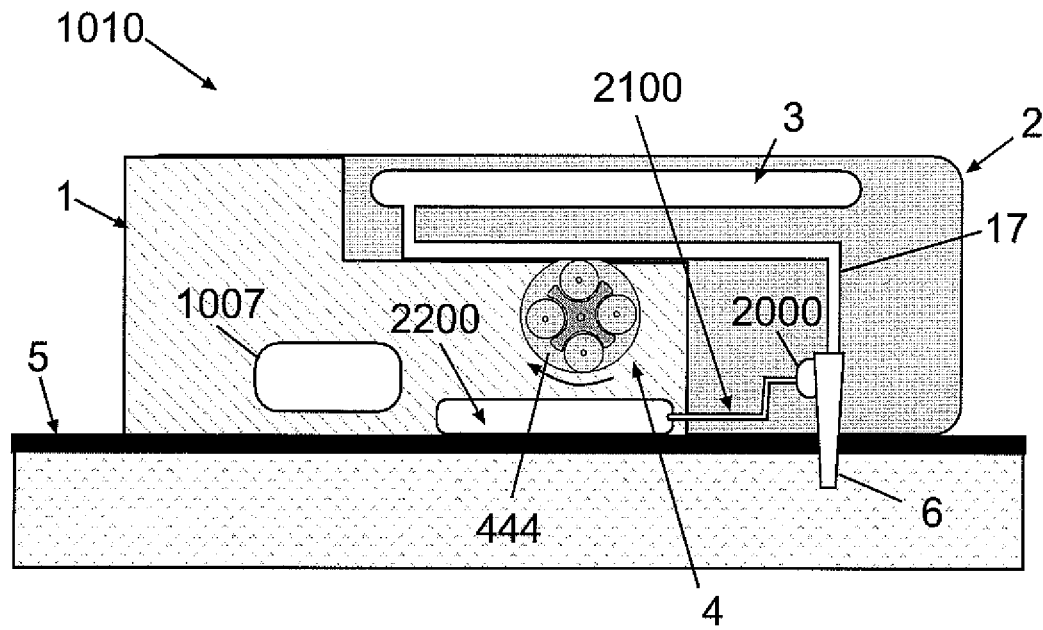
FIG. 7 are schematic diagrams showing a reciprocating system that is capable of dispensing fluid to the subcutaneous layer and transport analyte-enriched fluid from the subcutaneous layer to an external sensing element using one cannula that is associated either with (a) a peristaltic or (b) a piston pumping mechanism.
Figure 7B:
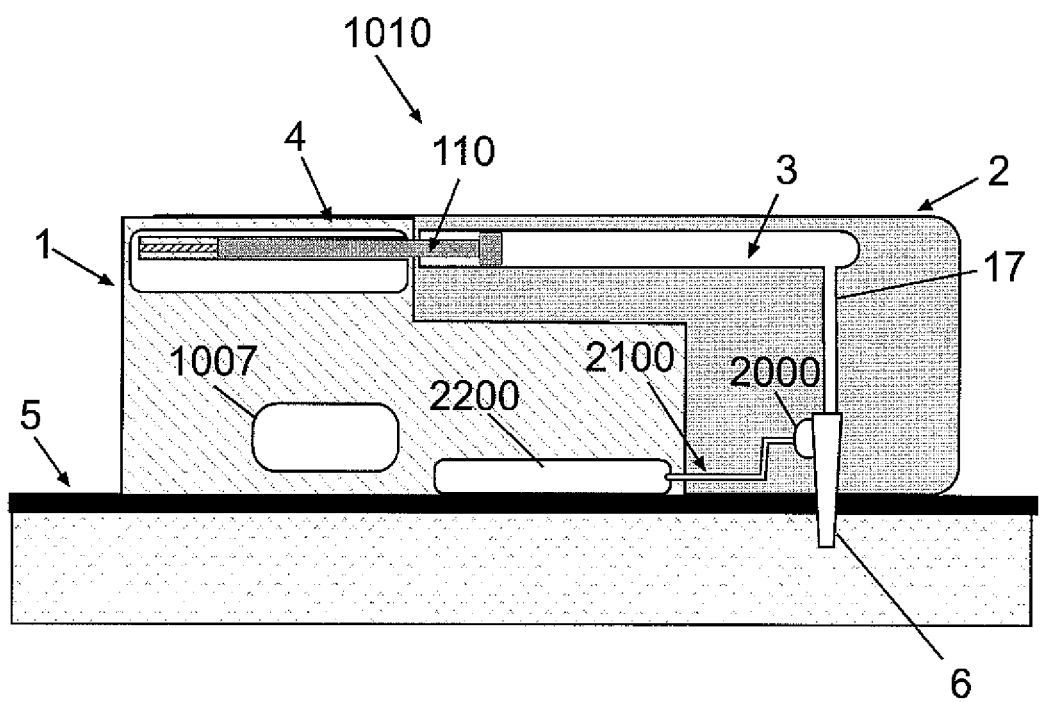

FIG. 7*a* shows an example of a pumping mechanism suitable for the reciprocating operation and having a peristaltic mechanism. Rotation of a rotary wheel 444 in one direction (clockwise according to the view of FIG. 7*a*) causes the delivery of fluid from the reservoir 3 into the body; rotation of the rotary wheel 444 in the opposite direction (counterclockwise) causes collection of the body constituents for sensing. The sensing apparatus includes a sensing element 2000, located in the disposable part 2; sensor processing elements 2200 located in the reusable part 1; wiring or other means for transferring signals through a linkage 2100 located in both the disposable 2 and reusable 1 parts. Certain components of the sensing element may be located in the reusable part 1. In the sensing apparatus, the rotary wheel 444 when rotated in the counterclockwise direction causes transfer of fluid from the body through the cannula 6 back into the sensing element 2000. FIG. 7*b* shows an example of a device employing a piston pumping mechanism 4 for the reciprocating operation. Operation of this device works in a similar manner to that shown in FIG. 7*a*. Forward and reverse motion of the fluid is controlled by extending or withdrawing the plunger 110 within the fluid reservoir 3.

Figure 8A:
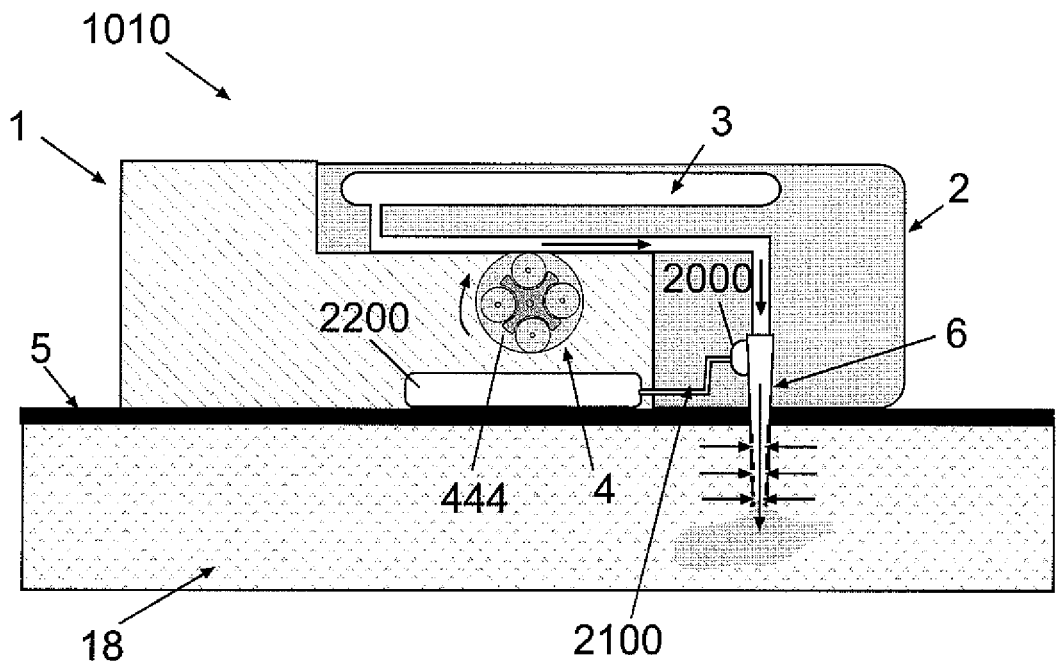
FIG. 8 are schematic diagrams showing a detailed view of a fluid reciprocating system within the two-part patch unit employing either (a) a peristaltic or (b) a piston pumping mechanism.

FIG. 8 shows two examples of a device provided with fluid reciprocating means and configured as a two-part, skin-adherable patch unit 1010. A single cannula 6 is employed, which is used for fluid (e.g. saline, insulin) dispensing and for analyte (e.g. glucose) sensing. As shown in FIG. 8*a*, fluid from the reservoir 3 is pumped, for example by a peristaltic pump 4, forward when the rotary wheel 444 of the pump is rotated, for example in the clockwise direction. In this situation the fluid is supplied into a subcutaneous compartment 18 in the body, through a cannula 6. Analyte molecules present in the interstitial fluid (ISF) within the subcutaneous compartment 18 diffuse, perfuse, permeate, or are otherwise transported across the semi-permeable or fully permeable wall of the cannula 6 into the fluid which resides within the cannula 6. The analyte-enriched fluid can be pumped backwards when the rotary wheel 444 is rotated in the opposite direction, for example counterclockwise, through the cannula towards a sensing element 2000 located above the skin 5, where analyte concentration levels are measured. The measured signal generated by the sensing element 2000 is transferred via an electrical wiring linkage or optical means 2100 to a sensor processing element 2200, where the measured signal is processed. The back and forth motion of the pumping mechanism 4, forward motion for delivering fluid into the subcutaneous compartment 18 and backward motion for pumping analyte-enriched fluid back from the subcutaneous compartment 18 to the sensing element 2000, constitutes the reciprocating operation.

Figure 8B:
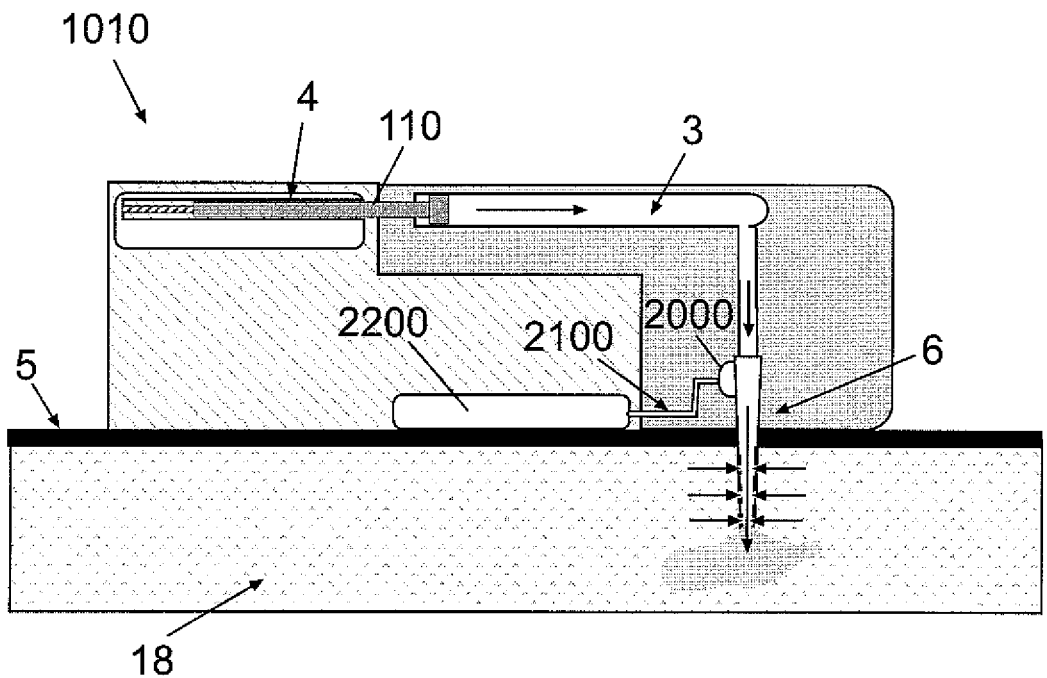

FIG. 8*b* shows an alternative configuration of this device in which the pumping mechanism 4 can be a syringe with a plunger 110. The plunger 110 can be pushed forward or pulled backward thus allowing the reciprocating operation. In this device the fluid reciprocating means is accommodated within the two-part patch unit 1010. A single cannula 6 is used for fluid (e.g. saline, insulin) dispensing and for analyte (e.g. glucose) sensing. Fluid from the reservoir 3 can be pumped forward and backward by the syringe pump 4.

Figure 9:
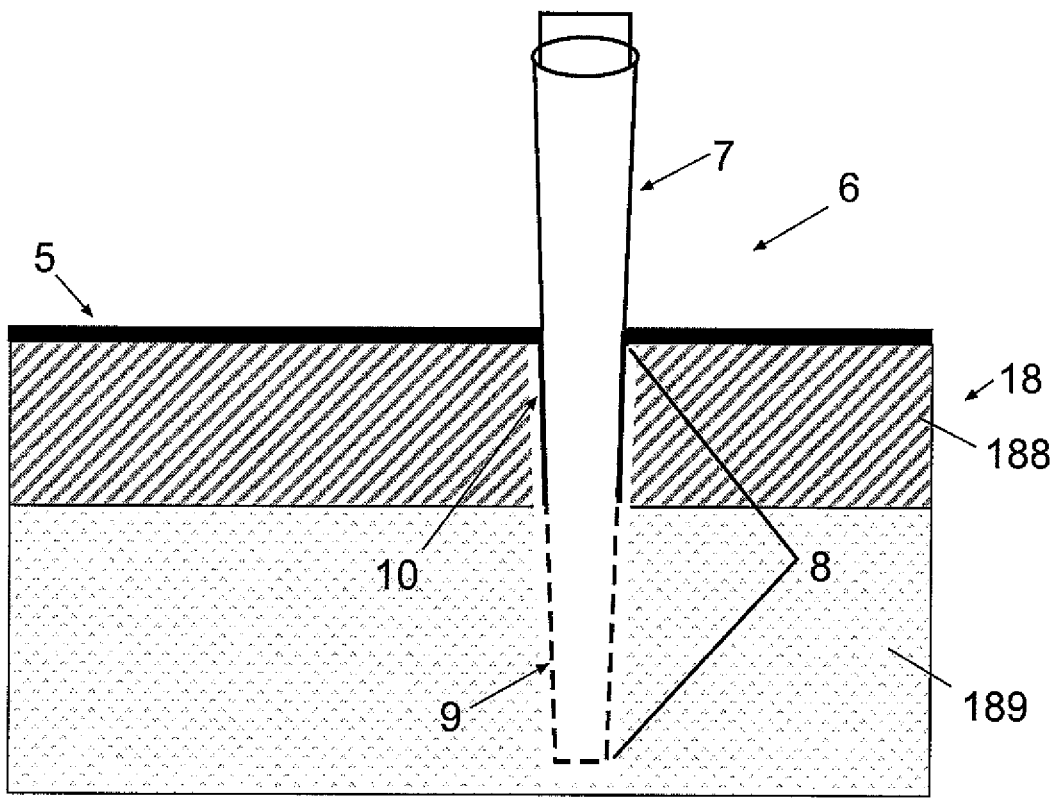
FIG. 9 is a schematic diagram showing a cannula structure and its location within the subcutaneous tissue.

FIG. 9 illustrates a possible structure of the cannula 6, with its upper 7 and lower 8 portions residing, respectively, above and below the skin surface 5. The location of the lower portion 8 of the cannula 6 is inside the bodily compartment 18. The bodily compartment 18 into which the lower portion 8 of the cannula 6 is inserted, is divided into a cutaneous compartment 188 and a subcutaneous compartment 189. The cutaneous compartment 188 generally contains no flow of analyte molecules, therefore no diffusion or transport into the interior volume of the cannula takes place in this compartment 188. The subcutaneous compartment 189 is rich in analyte and the diffusion or transport process may take place here. Thus, diffusion or transport of glucose molecules into the cannula 6 interior volume occurs only in the subcutaneous compartment 189.

The lower portion 8 can include two segments—a non-permeable segment 10, lying in the cutaneous compartment 188, and a lower segment 9 that is semi or fully permeable and that resides in the subcutaneous compartment 189 when the cannula is deployed into a user's body. The lower semi or fully permeable segment 9 allows diffusion or other transport of analyte (e.g. glucose) molecules in accordance with their concentration gradient, across the cannula 6 walls.

Figure 10A:
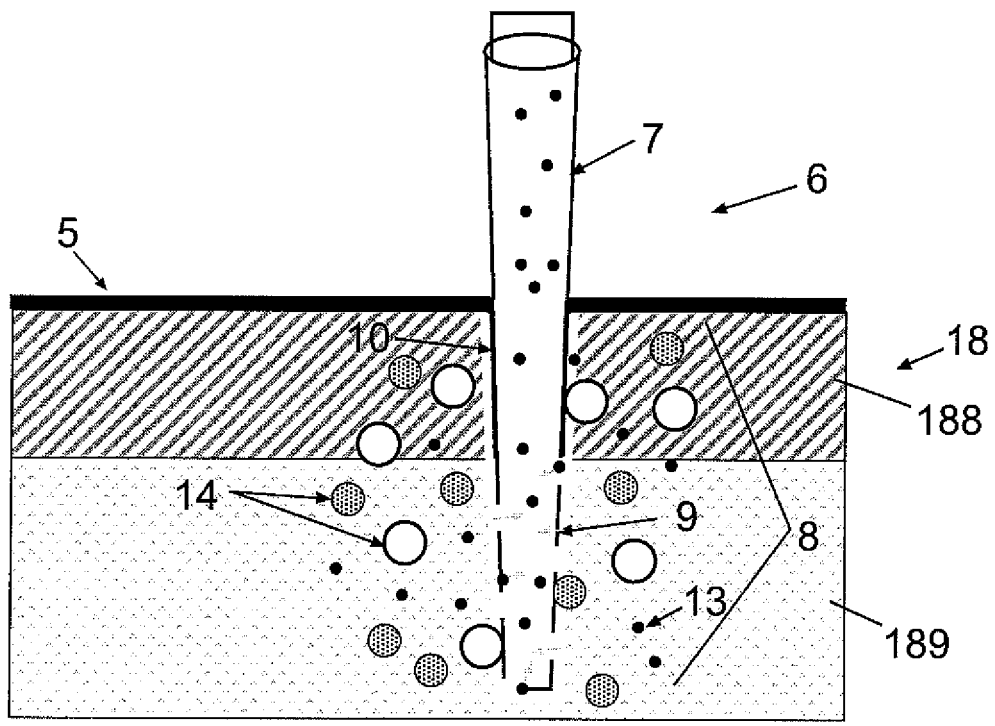
FIG. 10 are schematic diagrams showing an analyte diffusion or transport process taking place either through (a) a semi-permeable cannula or (b) a fully permeable cannula.

FIG. 10 illustrates a diffusion or transport process. As stated above the lower segment of the cannula 6 can be either semi or fully permeable. In FIG. 10*a*, the lower cannula portion 8 comprises a non-permeable region 10, residing in the upper cutaneous compartment 188 and a semi-permeable region 9, residing in the lower subcutaneous compartment 189. The wall of the lower region 9 of the cannula 6 functions as a membrane, which selectively allows analyte molecules of low molecular weight, and particularly, the desired analyte (e.g. glucose) 13 to pass through the pores of the membrane 9, while other compounds of higher molecular weight 14 do not pass through the pores. The cannula 6 can be perfused with fluid (e.g. saline, insulin) in order for diffusion or other transport to occur across the semi-permeable membrane 9. Diffusion occurs in the direction of analyte concentration gradient, between the interstitial fluid (ISF) in the lower subcutaneous compartment 189 and the fluid within the cannula 6. Establishing of analyte concentration equilibrium (full recovery) or partial recovery between the interior and exterior regions of the cannula 6 depends on recovery time, which depends on the duration of the "diffusion phase." The outcome of the diffusion process is the presence of a fluid within the cannula 6, which is enriched by the analyte. In this fluid, the analyte concentration is proportional or equal to the analyte concentration in the ISF depending on the recovery time. The analyte-enriched fluid inside the cannula 6 can now be transported to a sensing element located above the skin 5. This can be carried out by means of the reciprocating operation of the pumping mechanism.

Figure 10B:
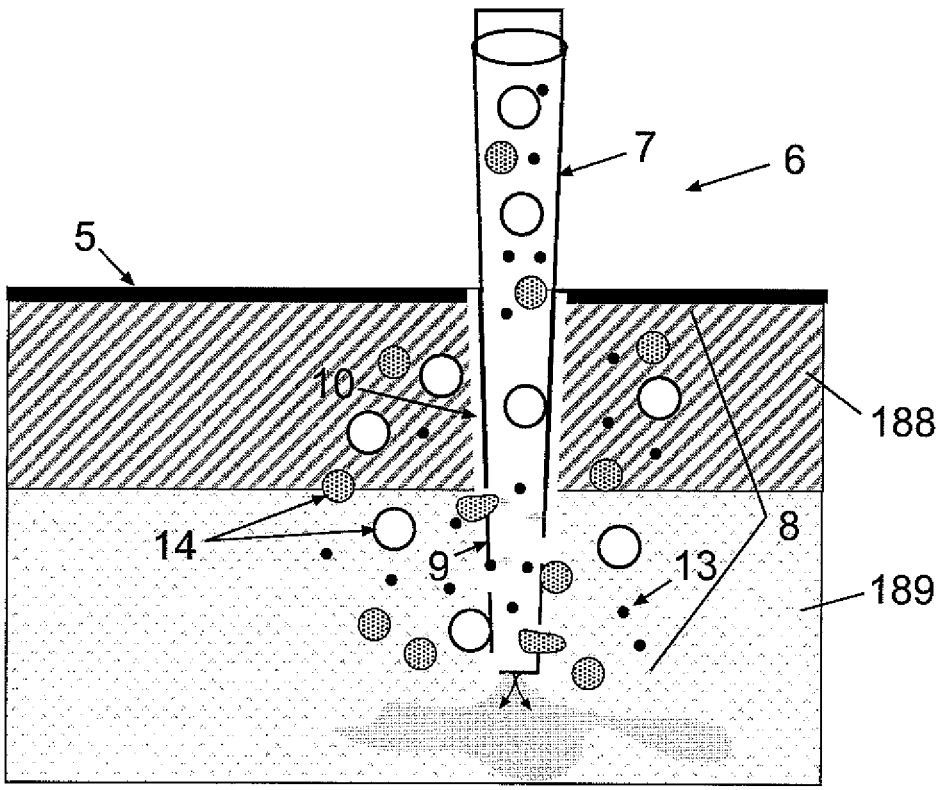

In another preferred embodiment of the invention, the cannula 6 that is used for sensing analyte concentration levels and for delivering fluid is fully-permeable, i.e. allows for nonselective diffusion of molecules of analytes into the cannula 6. In FIG. 10*b*, the lower cannula portion 8 comprises a non-permeable region 10, residing in the upper, cutaneous compartment 188, and a fully permeable region 9, residing in the lower subcutaneous compartment 189. The wall of the fully permeable region 9 constitutes a membrane, whose pores allow small analyte molecules (i.e. glucose) 13 and larger molecules of other compounds 14 from within the ISF to non-selectively pass therethrough thus allowing for a faster diffusion or transport process. The cannula 6 is perfused with an isotonic solution (e.g. insulin, saline) in order for diffusion or transport to occur. For example, if the isotonic solution is initially completely free of the measured analyte (e.g. glucose), the molecules of glucose from within the ISF follow the concentration gradient and diffuse into the cannula 6. In this configuration, if insulin is used as the perfused fluid, insulin molecules may diffuse out through the large pores of the permeable membrane 9 of the cannula 6, to the body.

Figure 11A:
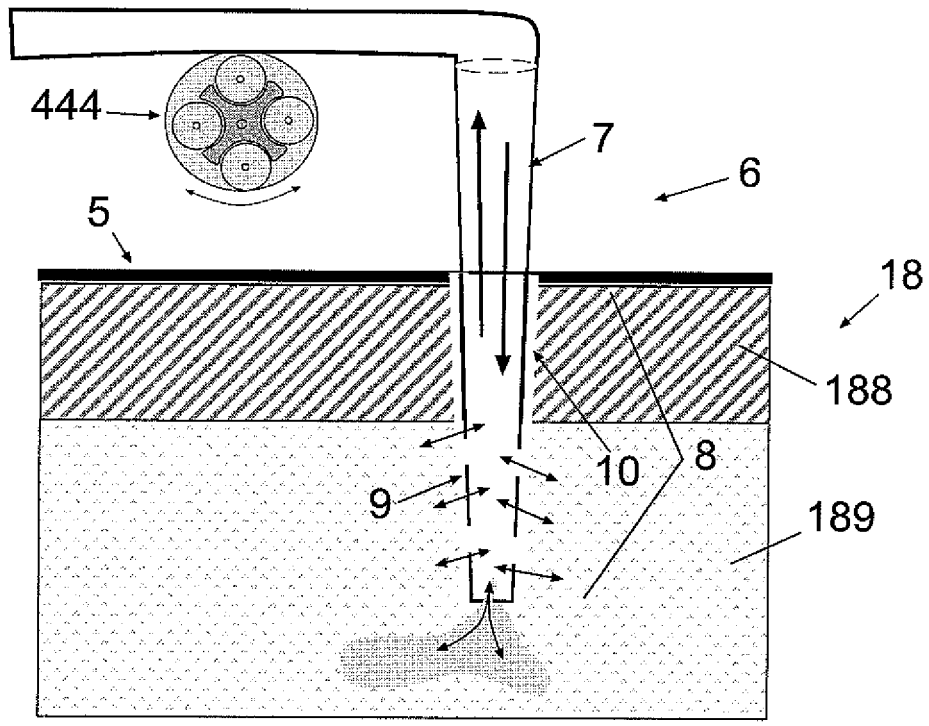
FIG. 11 are schematic diagrams showing directions of fluid motion through a cannula, when either (a) a peristaltic or (b) a piston pumping mechanism is employed.
Figure 11B:
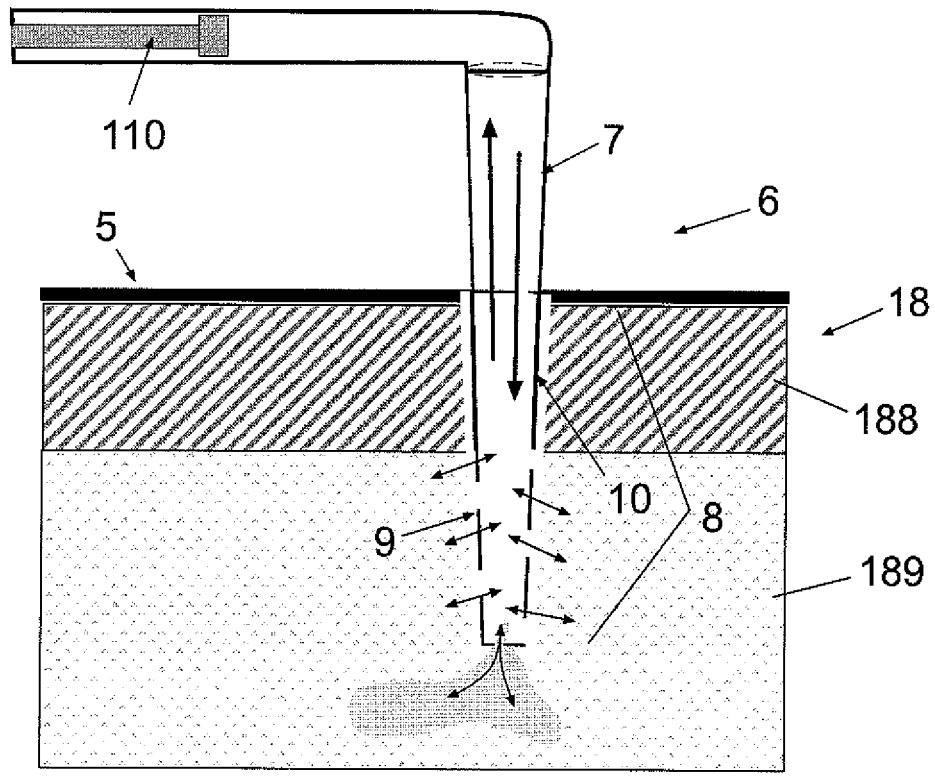

FIG. 11 shows the possible directions of fluid motion through the cannula 6. In FIG. 11*a*, a rotary wheel 444 alternately rotates clockwise and counterclockwise and accordingly allows reciprocating operation during which the fluid can be delivered forward and backward to and from the subcutaneous cannula. The pumping mechanism can alternatively be a syringe with a plunger 110, as shown in FIG. 11*b* and discussed in greater detail above. The plunger 110 can be pushed forward or pulled backward thus allowing the reciprocating operation. Analyte-free fluid (e.g. saline, insulin) is delivered to the subcutaneous compartment 18 through the cannula 6 in a forward direction. Analyte diffusion or other transport across the semi or fully permeable cannula walls occurs. Subsequently, the analyte-enriched fluid is pumped backwards, towards a sensing element, located above the skin 5, where the analyte concentration is measured.

In some implementations, insulin can be pumped forward and glucose-enriched insulin can be pumped backwards to be withdrawn from the subcutaneous compartment into proximity with the sensing means. Other fluids besides insulin can be dispensed by the reciprocating means and the analyte may be any constituent from within the ISF. For example, saline, or another physiological solution, can be pumped forward and glucose-enriched fluid or fluid enriched with one or more other analytes can be pumped backwards.

Figure 12:
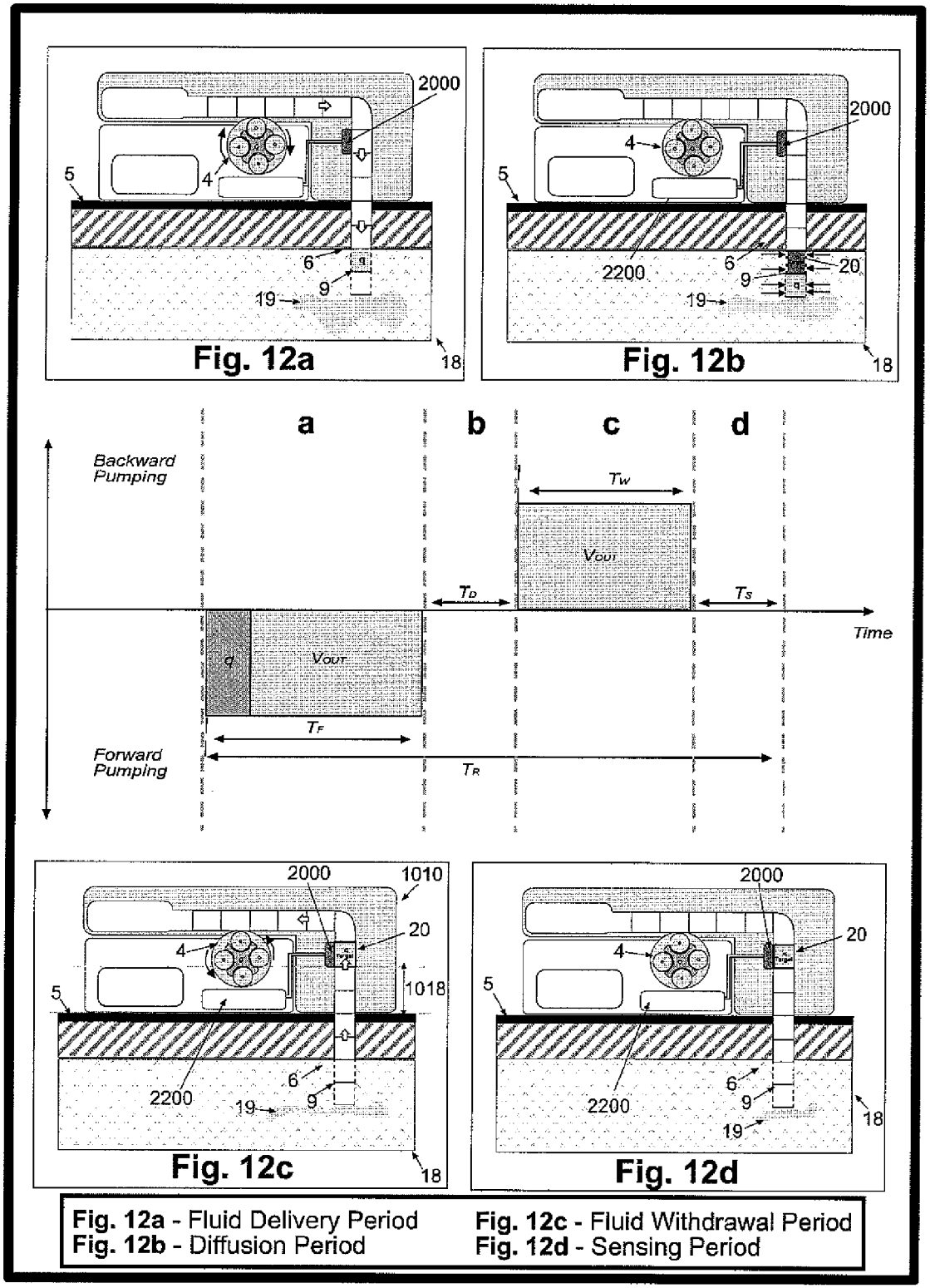
FIG. 12 are schematic diagrams showing associated time diagram for forward and backward pumping directions, and associated with the four phases of the reciprocating cycle: (a) fluid delivery, (b) diffusion, (c) fluid withdrawal, and (d) sensing.

FIG. 12 shows the reciprocating cycle, broken down to the main phases of the reciprocating operation, and their corresponding sequence and duration in time for a dispensing and sensing mechanism including a peristaltic pump. A similar sequence can occur for a syringe/plunger type pumping mechanism, a piezoelectric pumping mechanism, or the like. A reciprocating cycle can include the following phases: 1) a fluid delivery phase in which insulin is delivered into the body via forward pumping; 2) a diffusion phase in which diffusion of glucose (or other analyte) molecules occurs between the subcutaneous compartment and the fluid residing in the intra-cannula space while fluid pumping is halted; 3) a fluid withdrawal phase in which glucose-enriched fluid is withdrawn through the cannula towards a sensing element by virtue of backward pumping; and 4) a sensing phase in which glucose-enriched (or other analyte-enriched) fluid that has reached the sensing element is sensed, measured, analyzed, and ISF glucose (or other analyte) concentration levels are determined while fluid pumping is halted.

The phases of the reciprocating cycle can be performed as described below in reference to FIGS. 12a-12d. During the fluid delivery phase shown in FIG. 12a, fluid is pumped forward and delivered through the cannula 6 into the subcutaneous compartment 18. A depot of the fluid 19 is created subcutaneously and it may increase in size during the fluid delivery phase. The fluid is pumped forward into the body by the pumping mechanism 4. A single step (predefined movement) of the pumping mechanism 4, delivers a predetermined volume of fluid, defined as a quantum (q). Consecutive pumping steps deliver several fluid quanta. If the dispensed fluid is insulin, the number of quanta pumped into the body during each delivery phase is defined according to a required dose (for example a basal rate).

During the diffusion phase shown in FIG. 12b, pumping is halted and analyte molecules diffuse or are otherwise transported across the cannula 6 wall, between the ISF and the fluid residing inside the cannula. The subcutaneous portion of the cannula wall constitutes a semi or fully permeable membrane 9 that allows diffusion or other transport of analyte molecules according to their concentration gradient. During this phase the pumping mechanism is not active and thus it is in a "static state." At the end of the diffusion phase, full or partial equilibrium ("recovery") is established between the analyte concentration in the ISF and the analyte concentration inside the cannula 6 space. At the end of the diffusion phase, the fluid inside the cannula 6 is analyte-enriched fluid (such as for example glucose-enriched saline, glucose-enriched insulin).

During the fluid withdrawal phase shown in FIG. 12c, fluid is pumped backwards, and analyte-enriched fluid is pumped towards the sensing element 2000, located in the patch unit 1010 above the skin surface 5. During the backward pumping, fluid from the depot 19 is also pumped back, thus the size of the depot 19 is reduced.

During the sensing phase shown in FIG. 12d, pumping is again halted, and the sensing element 2000 measures the analyte concentration levels within the analyte-enriched fluid. During the sensing phase, the pumping mechanism 4 is again in a "static state."

In case of partial equilibrium (recovery <100%) the true analyte concentration is mathematically calculated using a "correction-prediction" algorithm as disclosed in greater detail below. Algorithms for calculating the actual percent of recovery can be based on the ratio between the actual diffusion time that took place in the system and the assumed diffusion time which would be required to reach full recovery. For example, in some implementations, partial recovery can be calculated using the so-called ionic reference technique in which ions serve as an endogenous marker for the estimation of the recovery (*Am. J. Physiol. Endocrinol. Metab.*, Vol. 276, Issue 2, E401-E408, February 1999). The ionic reference technique is a calibration method based on diffusion of ISF ions and glucose (e.g. K, Zn, Ca, Mg, etc) into the cannula. Because ions (of a known ISF concentration) and glucose diffuse at the same rate (both are small molecules), a simple mathematical ratio can be used to calculate glucose concentrations in the interstitial fluid according to ionic and glucose concentrations in the perfused fluid, after the diffusion process.

Figure 13:
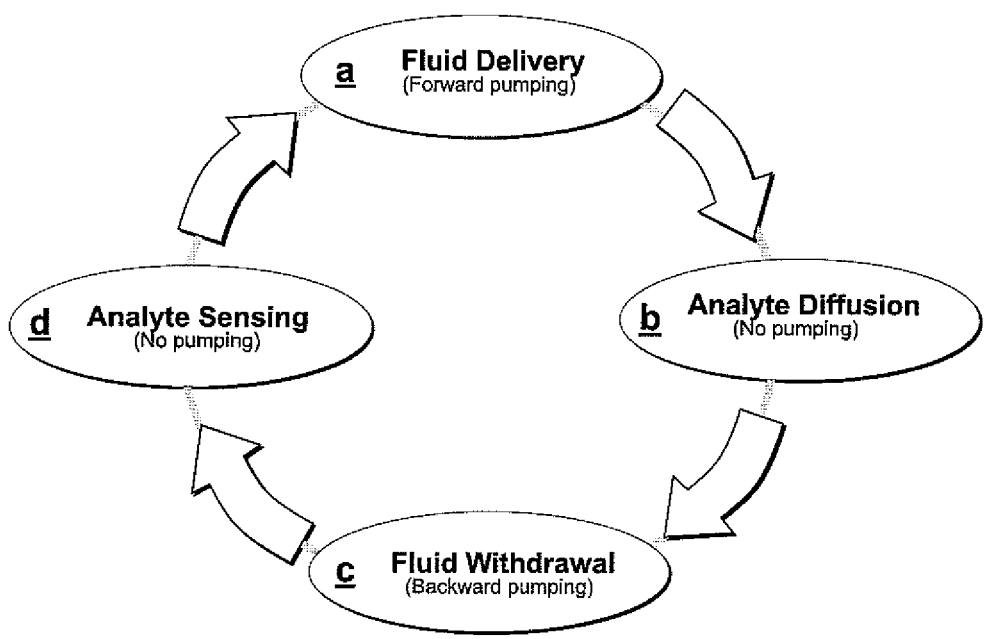
FIG. 13 is a process flow chart showing four phases of the reciprocating cycle: (a) fluid delivery, (b) diffusion, (c) fluid withdrawal, and (d) sensing.
Figure 14:
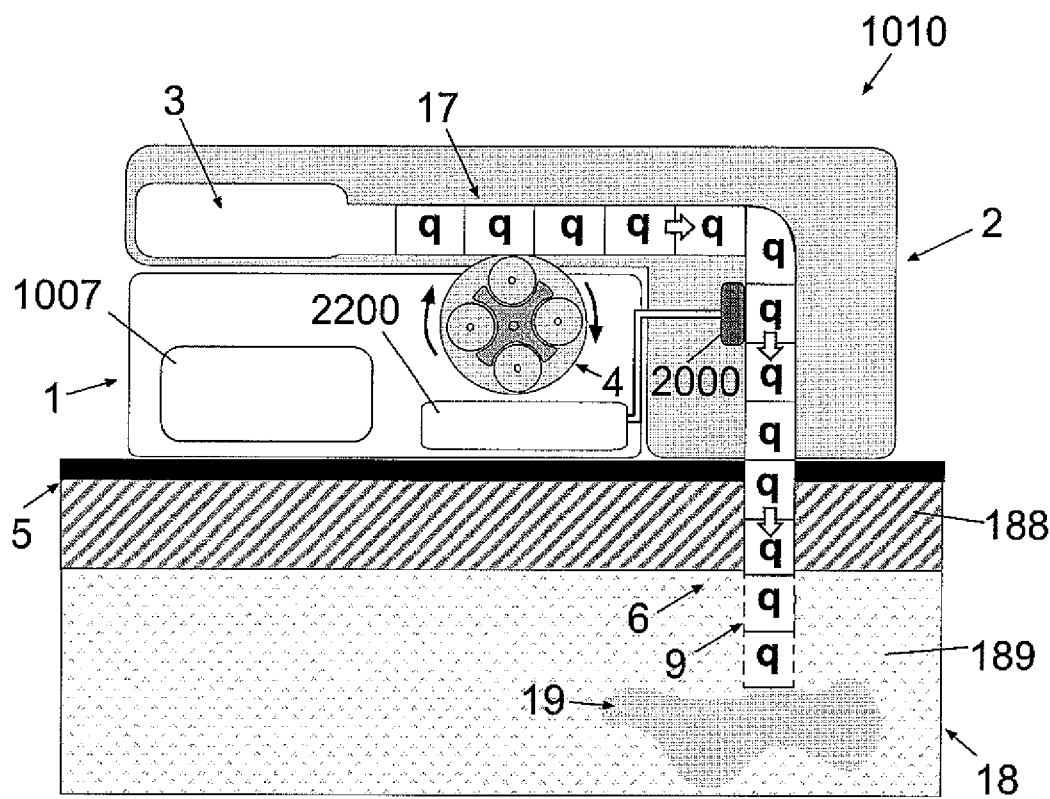
FIG. 14 is a schematic diagram showing additional detail of a fluid delivery phase.

FIG. 13 shows a schematic diagram of the reciprocating cycle, depicting the 4 phases of the reciprocating cycle and pumping directions. FIGS. 14-17 show each phase of the reciprocating cycle. During the fluid delivery phase, which is illustrated in FIG. 14, a predetermined volume of fluid is pumped forward into the body, during a predetermined period of time. The fluid inside the cannula 6 is schematically divided into individual quanta, relating to a minimal unit volume of fluid that is delivered in a single pumping step, defined as a quantum (q). Pumping in the forward direction delivers fluid into the body. The size of the fluid depot 19 increases. The duration of the fluid delivery phase, and the volume of delivered insulin corresponds to the user's insulin dose requirements.

Figure 15:
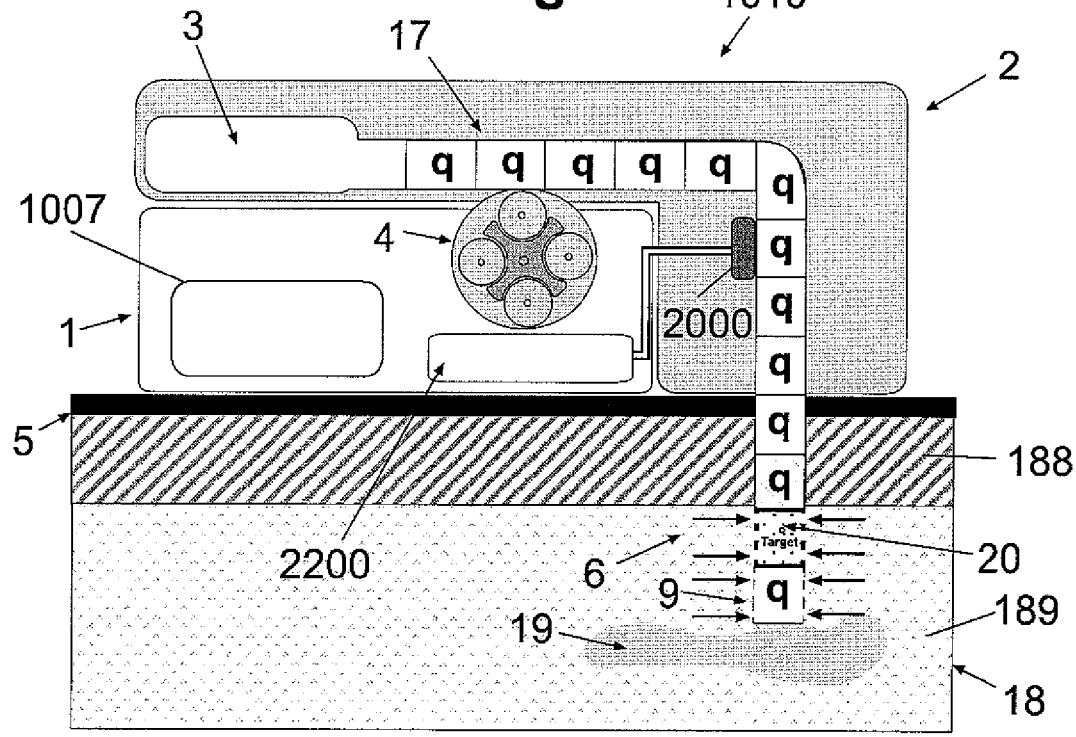
FIG. 15 is a schematic diagram showing additional detail of a diffusion phase.

During the diffusion or transport phase, which is shown in FIG. 15, analyte diffusion occurs in the subcutaneous compartment and the pumping mechanism 4 is in a "static state." Analyte molecules diffuse or are otherwise transported across the cannula membrane 9 according to the concentration gradient. At the end of the diffusion or transport phase, at least one quantum in the cannula 6 contains analyte-rich fluid, and serves as the quantum to be analyzed. The quantum that contains the analyte-rich fluid is referred-to as the target quantum, $q_{target}$ 20. Due to fluid absorption by the body that occurs throughout the duration of the diffusion phase, the depot size 19 may decrease in size. The duration of the diffusion or transport phase can be determined by the time interval set between the fluid delivery phase and the fluid withdrawal phase. A complete recovery (100%) is achieved if this time interval is set to exceed the time required for establishing concentration equilibrium.

The sensing element 2000, which measures analyte concentration in the analyte-enriched fluid, is located in the patch unit 1010 above the skin 5. Therefore, during the next phase, the analyte-rich, subcutaneous, target quantum ($q_{target}$) can be pumped backward across the cutaneous compartment 188 and past any device dead space 1018 above the skin 5 until the target quantum reaches the sensing element 2000. This is done during the fluid withdrawal phase, during which the fluid depot 19 may gradually decrease in size as it enters the cannula 6.

Figure 16:
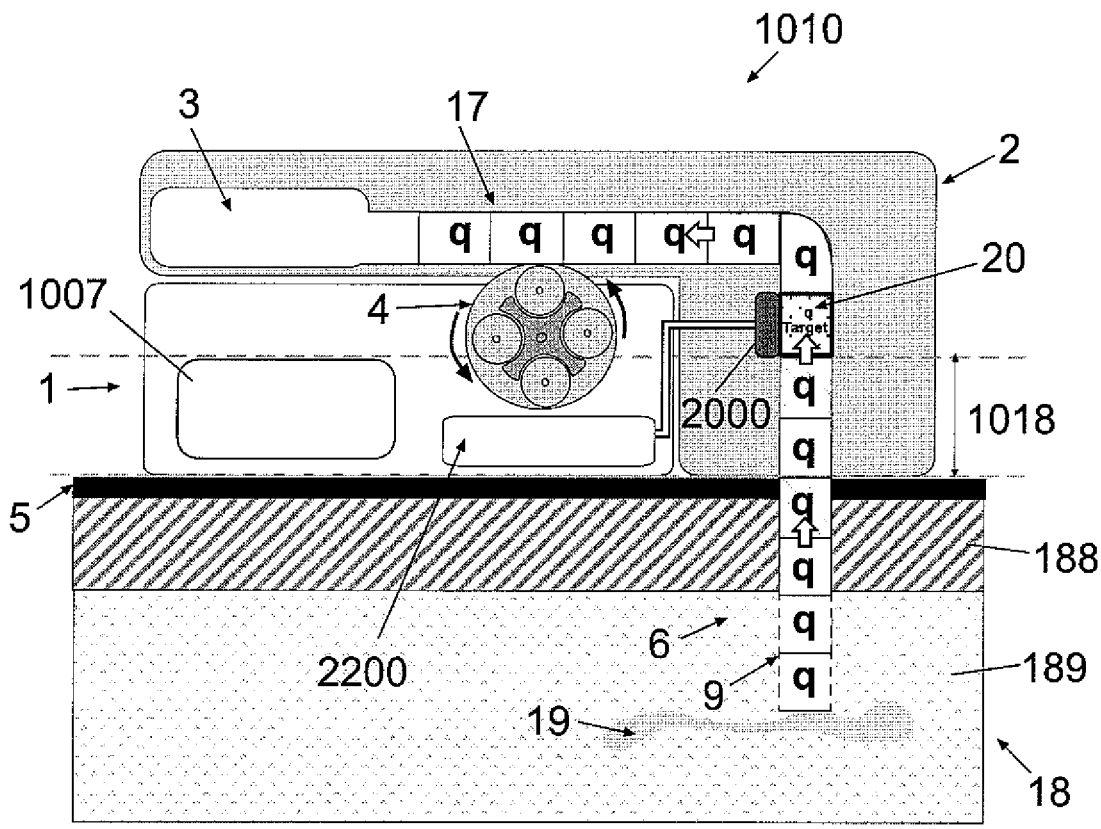
FIG. 16 is a schematic diagram showing additional detail of a fluid withdrawal phase.
Figure 17:
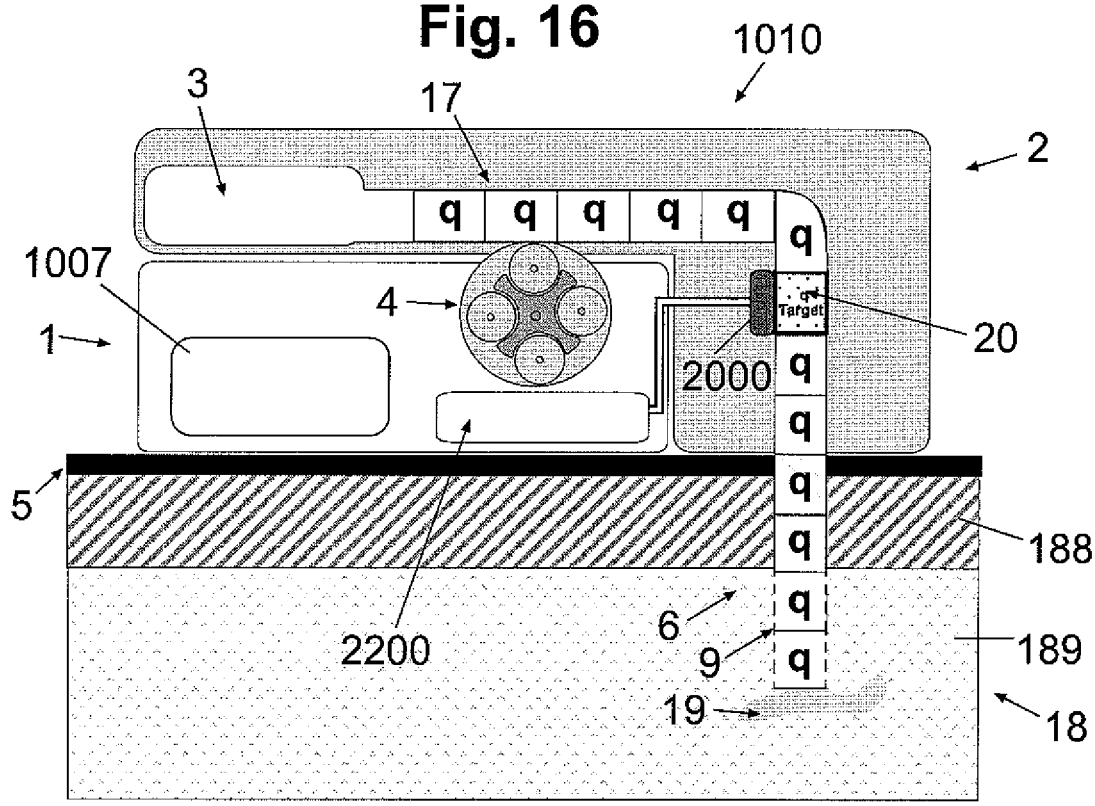
FIG. 17 is a schematic diagram showing additional detail of a sensing phase.

FIG. 16 shows the target quantum, $q_{target}$ 20, near the sensing element 2000, after being delivered by the backward pumping 4 during the fluid withdrawal phase.

Once the target quantum, $q_{target}$ 20, has reached the sensing element 2000, the pumping mechanism 4 halts pumping and shifts to a "static state". The sensing phase occurs, during which the analyte-enriched fluid is analyzed by the sensing element 2000, as shown in FIG. 16. For sensing analyte the concentration levels of the analyte, the sensing element can be use electrochemical, optical, or other sensing technologies. Among other options, electrochemical glucose sensors can include enzyme-catalyzed oxidation using amperometric or potentiometric operating principles. Optical sensing methods can include near-infrared (NIR), infrared (IR), Raman, polarimetry, and photoacoustic technology or the like. In NIR spectroscopy, for example, a selected band of NIR radiation is transmitted through the sample, and analyte concentration is obtained by spectral analysis.

Figure 18A:
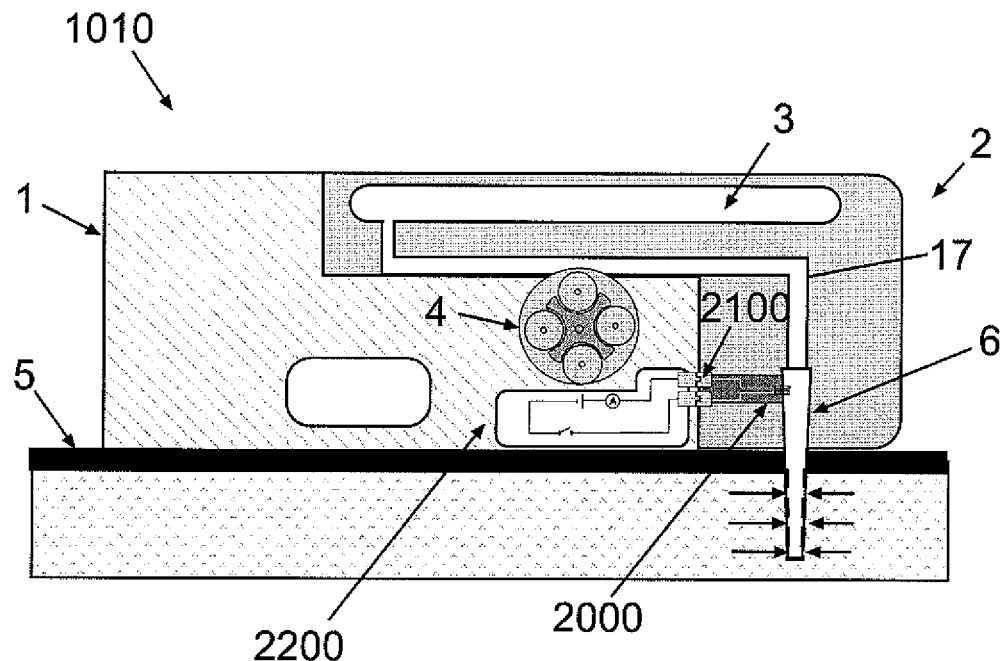
FIG. 18 are schematic diagrams showing (a) a general view of a system employing electrochemical sensing and (b) an exploded view of sensing system components.

In various implementations of the reciprocating system, the sensing can be performed using electrochemical detection. FIG. 18a shows an embodiment of a reciprocating system residing in a two-part patch unit 1010, in which the sensing element 2000, located in the disposable part 2, contains electrochemical electrodes. An electrical signal, such as for example current, voltage, or the like, can be induced by analyte oxidation taking place on the electrodes. This electrical signal can be transferred via electrical wiring or any other suitable signal transferring means 2100 to the sensor processing elements 2200 located in the reusable part 1.

Figure 18B:
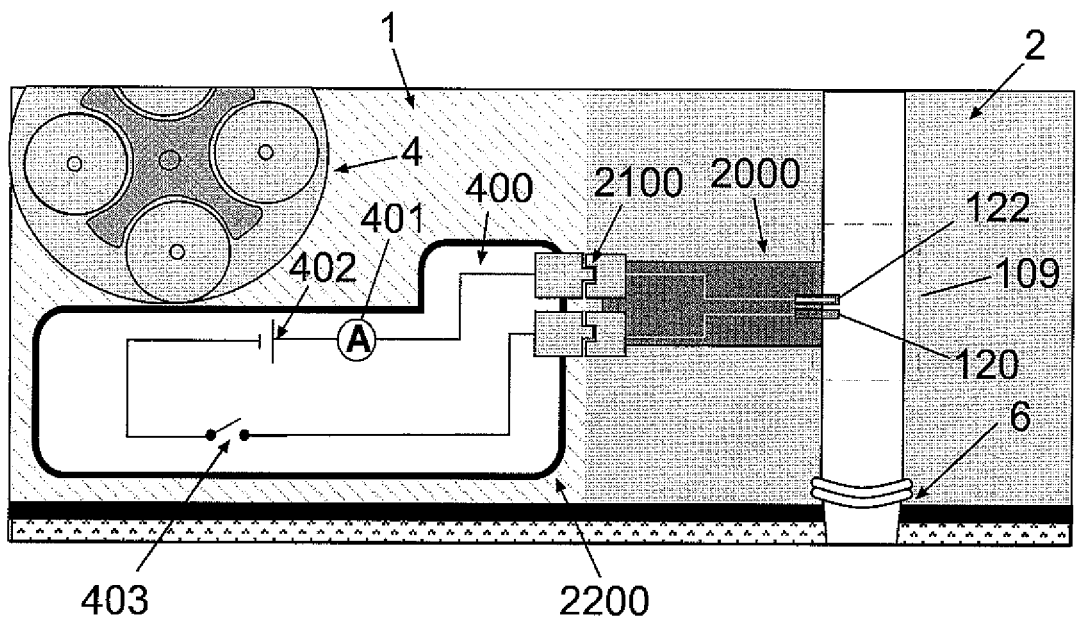

FIG. 18b shows an enlarged view of the electrochemical sensing means. In one preferred embodiment, the electrochemical sensing means contains a circuit 400, that may contain at least one amperometer 401, at least one power supply 402, and a switch 403. The sensing element can contain at least one working electrode 122 and at least one counter electrode 120. A reference electrode can be present as well. Electrons from the working electrode 122 of the sensing element 2000, flow towards the positive pole of a power supply 402 and the current is measured by an amperometer 401. A switch 403 can open and close the circuit when needed so that current passes through the circuit 400 only when measurements are carried out, thus saving energy.

The working electrode 122 is the electrode on which the electrochemical reaction takes place. An enzyme, such as for example GOX, hexokinase, glucose dehydrogenase, or the like, which catalyzes the oxidation of the analyte, is deposited on the working electrode. The oxidation can be effected with the assistance of a mediator, such as for example an electron transfer agent. In the oxidation-reduction (redox) reaction taking place on the working electrode, at least one electron is transferred for each oxidized analyte molecule. Amperometric detection is based on measuring the transferred electrons of an electro-active compound at a working electrode.

A counter electrode 120 can be paired with the working electrode 122. An ion current can be passed through the analyte enriched solution between the two electrodes. Additionally, a reference electrode can be used in measuring the working electrode potential. A reference electrode generally has a constant electrochemical potential because no current flows through it.

Figure 19A:
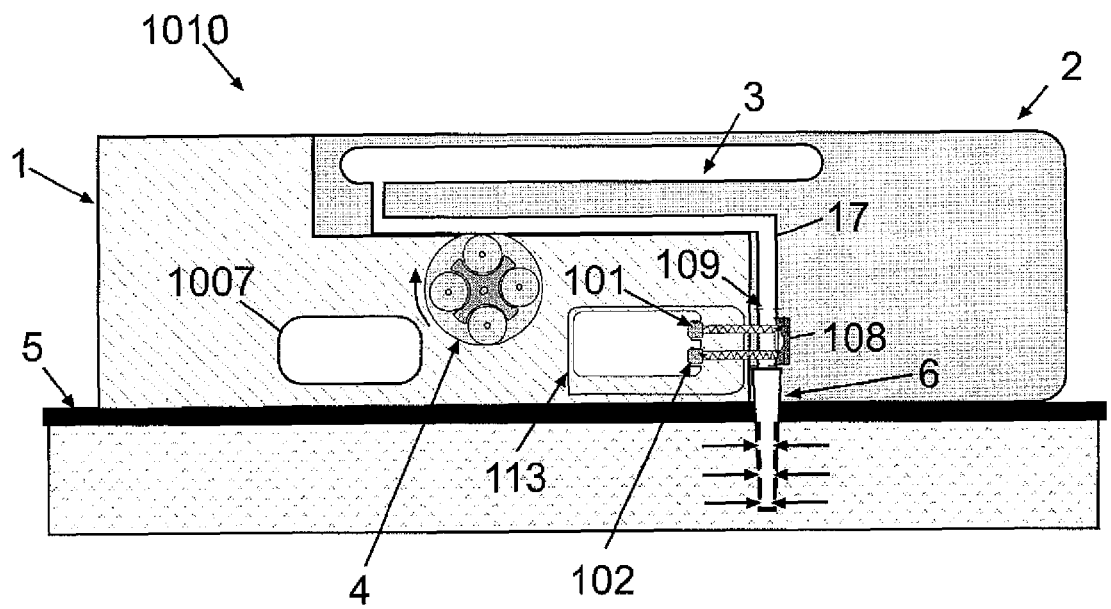
FIG. 19 are schematic diagrams showing (a) a general view of a system employing spectroscopic sensing and (b) an exploded view of the sensing means.

In some implementations of the device provided with the reciprocating system, the sensing can be accomplished using a spectroscopic detector. FIG. 19a shows an embodiment of a reciprocating system residing in a two-part patch unit 1010, in which the sensing element is optics-based. A spectrometer 113 within the reusable part 1 can contain a source 101 of electromagnetic radiation and/or energy and a detector 102. Emitted electromagnetic radiation and/or energy passes through the measuring cell 109 provided in the disposable part 2, is reflected back by the deflector 108, and then detected by the detector 102. The detected electromagnetic radiation and/or energy is then analyzed.

Figure 19B:
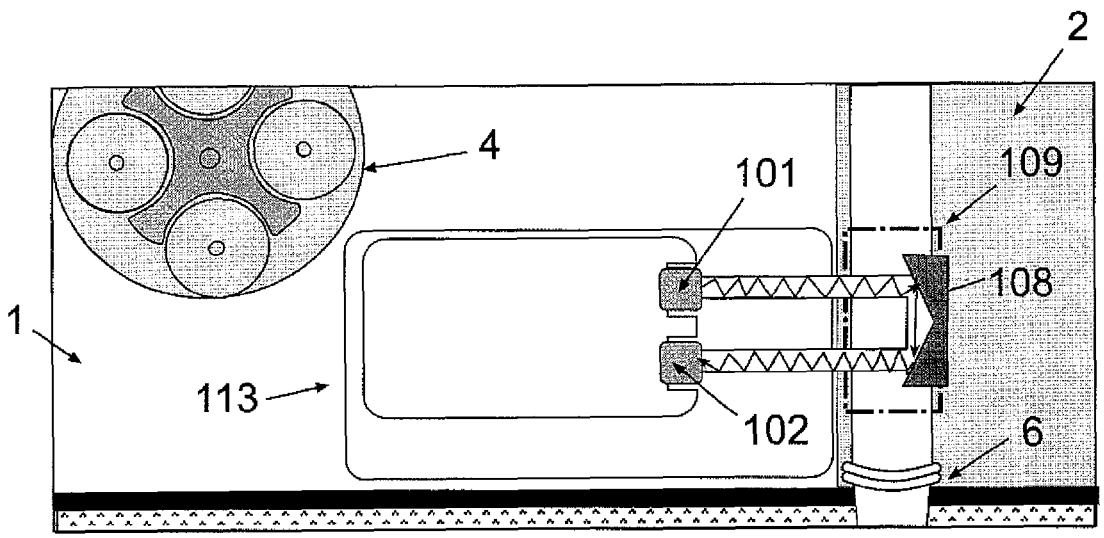

FIG. 19b shows an exploded view of a spectroscopic sensor. A electromagnetic radiation and/or energy emitting source 101 emits electromagnetic radiation and/or energy to be detected by a single detector 102. Electromagnetic radiation and/or energy is transmitted from the source 101, located in the reusable part 1 of the patch unit. The electromagnetic radiation and/or energy can be transmitted via an optical device, such as for example a fiber or one or more mirrors, to the measurement cell 109 that is located in the disposable part 2. The transmitted electromagnetic radiation and/or energy passes through the analyte-rich solution, residing in the measurement cell 109, eventually reaching the detector 102, located in the reusable part 1. Before reaching the detector the electromagnetic radiation and/or energy spectrum can optionally be separated by a grating and analyzed by separate detectors. Spectral analyte analysis can optionally be done by the use of more than one electromagnetic radiation and/or energy emitting source and more than one detector corresponding to various wavelengths and frequencies.

The volumes of fluid transferred during the cycle of the reciprocating operation can be determined by one or more factors. The amount of fluid pumped forward during the fluid delivery phase can optionally be larger than the amount of fluid pumped backwards during the fluid withdrawal phase. The net amount of fluid that remains in the body, after the fluid delivery, diffusion, and fluid withdrawal phases, can be set to meets the user's standard requirement, such as for example as an insulin basal dose. Thus, the volume of delivered fluid in the fluid delivery phase depends on the user's requirement, absorbed fluid volume during the diffusion phase and pumped back volume in the fluid withdrawal phase. Fluid absorption can have inter- and intra-individual variability, for example the rate of insulin absorbance depends on insulin type, insulin sensitivity, on insertion site, etc.

Figure 20:
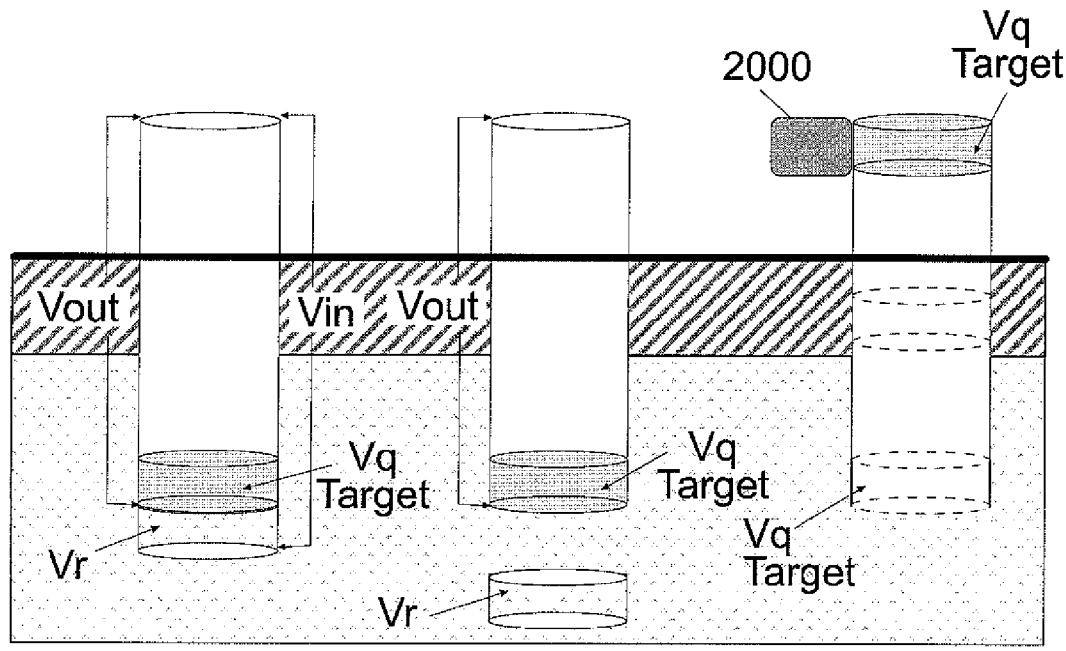
FIG. 20 is a schematic diagram showing the volumes $V_{in}$, $V_{out}$, and $V_r$.

The volume needed to be pumped backwards ($V_{OUT}$) should allow $q_{target}$ to reach the sensing element 2000. This volume generally includes the volume confined between $q_{target}$ and the sensing element 2000, including the volume corresponding to the sensing element and the volume of $q_{target}$ itself. These volumes are depicted in FIG. 20, in which $V_{IN}$ is the volume of fluid pumped into the body during the fluid delivery phase, $V_R$ is the volume of fluid required by the user, and $V_{OUT}$ is the volume of fluid pumped back from the body during the fluid withdrawal phase.

The volume of insulin pumped in the forward direction ($V_{IN}$) is determined by the volume to be pumped back in the fluid withdrawal phase ($V_{OUT}$) and the volume needed to be delivered into the body for therapy ($V_R$) as stated in equation 1:

$$V_{IN} = V_{OUT} + V_R \quad (1)$$

The number of quanta of fluid contained in each abovementioned volume is determined by several parameters: the required amount of fluid (for example insulin) needed to be delivered to the user's body per unit of time (which can be the insulin basal rate measured as units per hour), the diameter and length of the delivery tube and cannula, pumping mechanism characteristics, and the rate at which the pump operates.

In a fluid withdrawal phase, in which a predetermined volume of fluid is transported from the subcutaneous tissue to the sensing element, where analyte levels are measured, the total transported volume may be determined by the geometry of the cannula and the volume needed for measurement by the sensing element ($q_{target}$).

Figure 21:
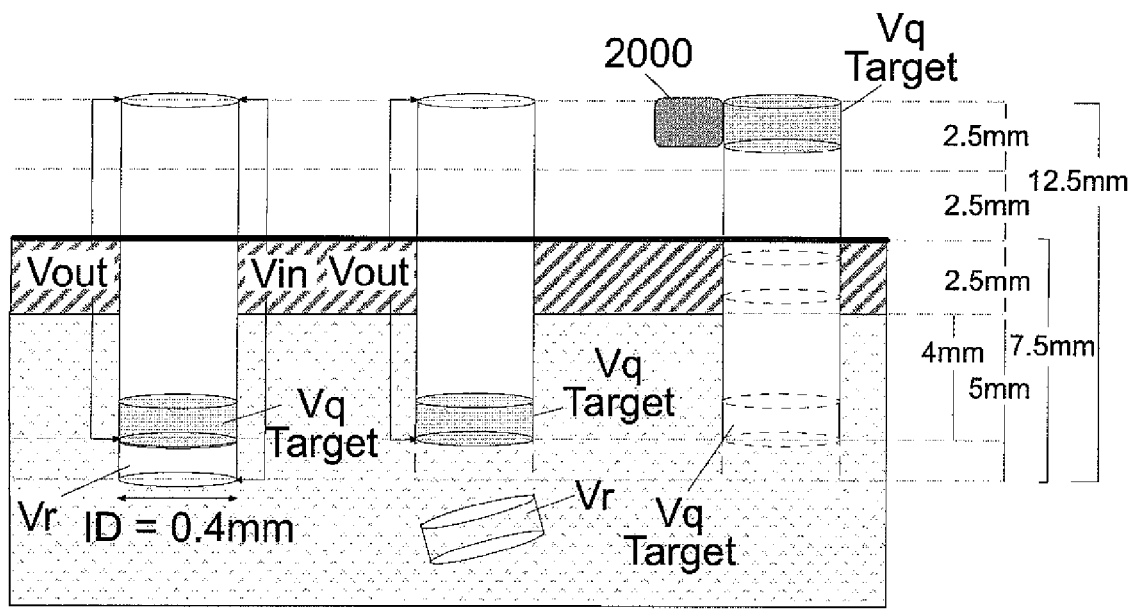
FIG. 21 is a schematic diagram showing a cannula with its geometrical dimensions.

A non-limiting, illustrative numerical example for calculating $V_{IN}$ and $V_{OUT}$, for a specific cannula length and diameter is now presented. FIG. 21 shows the cannula relevant for this numerical example, with given geometrical dimensions and volumes. The total length of the cannula, including dead space is 12.5 mm, which is split into several regions as follows: 2.5 mm vertical length of sensing cell, 2.5 mm length of device dead-space, 2.5 mm length of cutaneous compartment, and 5 mm length of subcutaneous compartment (of which 4 mm are relevant). The cannula inner diameter (ID) is 0.4 m. The length to be pumped backward (h) is the length of device dead-space added to the length of the cutaneous compartment and the length of the relevant subcutaneous compartment. In this example $$h = 2.5 \text{ mm} + 2.5 \text{ mm} + 4 \text{ mm} = 9 \text{ mm} \quad (2)$$

Using h, the volume needed to be pumped in the reverse or backward direction is given by $$V_{OUT} = \pi r^2 h = \pi (0.2)^2 \times 9 = 1.13 \text{ μl}, \quad (3)$$

and assuming that $V_R=1$ µl, the amount of fluid to be pumped in the forward direction is given by $$V_{IN}=V_{OUT}+V_R=1.13 \text{ µl}+1 \text{ µl}=2.13 \text{ µl} \tag{4}$$

For example if the fluid is rapid-acting insulin then 1 µl corresponds to 1 IU. Thus if the required insulin dose is 1 IU, the pump should deliver 2.13 IU and consequently the amount of fluid which the pump should deliver backward is 1.13 IU.

The fluid delivery and the analyte sensing are separated in time and not in space. For example, the fluid delivery and the analyte sensing (e.g. insulin delivery and glucose sensing) are carried out by pumping the fluid via the same place, via the same cannula. Duration of the forward and backward movements of the fluid carried out by the pump are selected in such a manner that the amount of delivered fluid (such as for example insulin) entering the body, and time provided for diffusion are sufficient for obtaining analyte-enriched fluid (e.g. glucose-rich solution). Fluid delivery phases occur every predetermined time, where this time is defined by the pumping mechanism.

Figure 22:
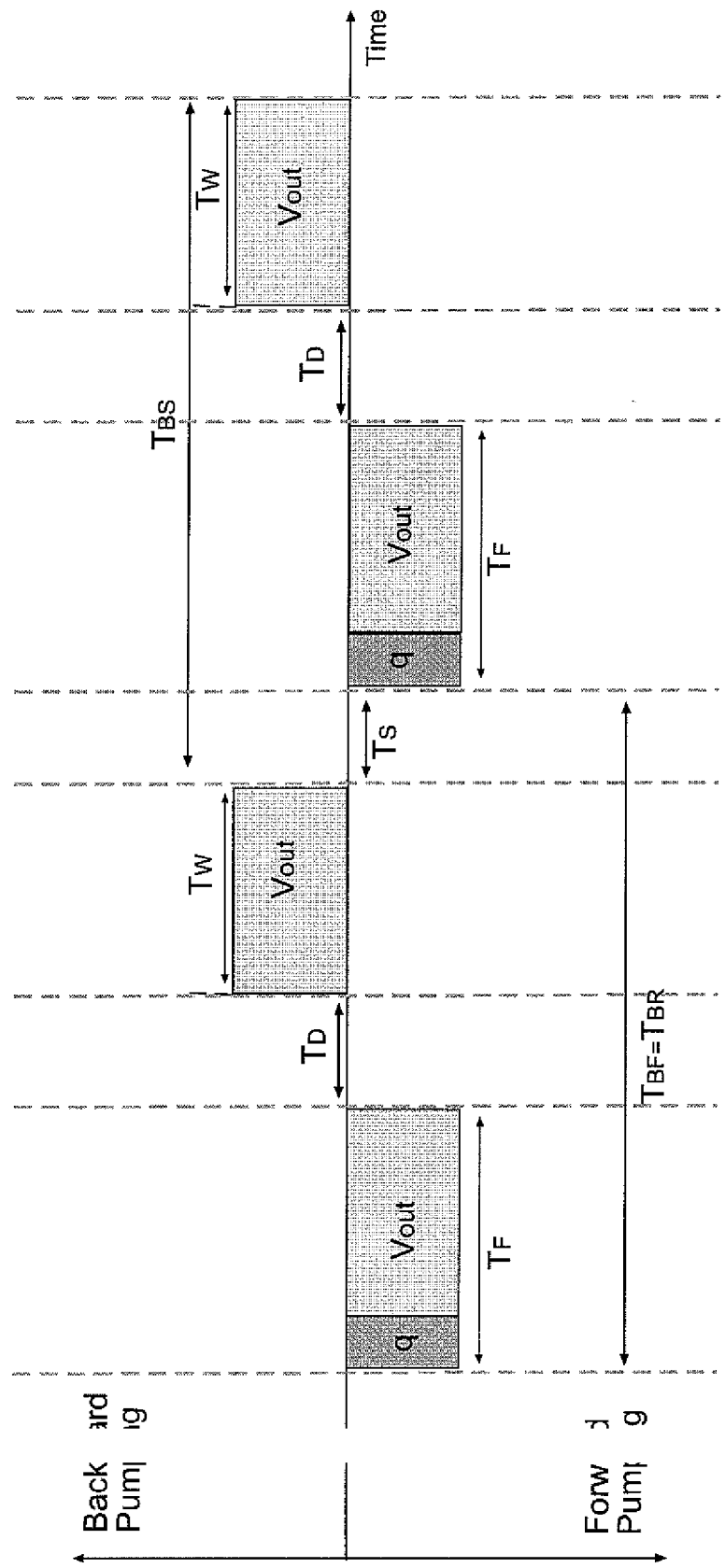
FIG. 22 is a time diagram associated with forward and backward directions of pumping, showing exemplary timings of fluid delivery, diffusion, fluid withdrawal, and sensing phases.

FIG. 22 shows a diagram of the forward and backward directions of pumping and timings of the fluid delivery, diffusion, fluid withdrawal, and sensing phases. Below are defined parameters, which will be used in the further disclosure. $T_F$ refers to the fluid delivery phase and is the time needed for forward pumping of volume $V_{IN}$. $T_D$ refers to the diffusion phase and is the diffusion time, while the pump is in a static state. $T_W$ refers to the fluid withdrawal phase and is the time needed for backward pumping of volume $V_{OUT}$. $T_S$ refers to the sensing phase and is the time needed to perform the sensing of the analyte-rich fluid by the sensing element. $T_{BF}$ is the time interval from the beginning of one fluid delivery phase to the beginning of a consecutive fluid delivery phase. $T_{BS}$ is the time interval from the beginning of one sensing phase to the beginning of a next consecutive sensing phase between two sensing phases. $T_{BR}$ is the time interval from the beginning of one reciprocating cycle to the beginning of a next consecutive reciprocating cycle. In the specific case shown in FIG. 22, $$T_{BF}=T_F+T_D+T_W+T_S. \tag{5}$$

In some implementations, fluid delivery phases may occur not within a reciprocating cycle. Thus, several fluid delivery phases may consecutively occur, even without an occurrence of a reciprocating cycle. Then after one or more independent fluid delivery phases, a reciprocating cycle might occur. In such an implementation, a cycle in which only a fluid delivery phase occurs will be referred-to further as a delivery cycle. During a delivery cycle, pumping is only carried out in a forward direction. The volume pumped during the delivery cycle ($V_{IN}$) (number of quanta) is determined by the required insulin dose.

Figure 23A:
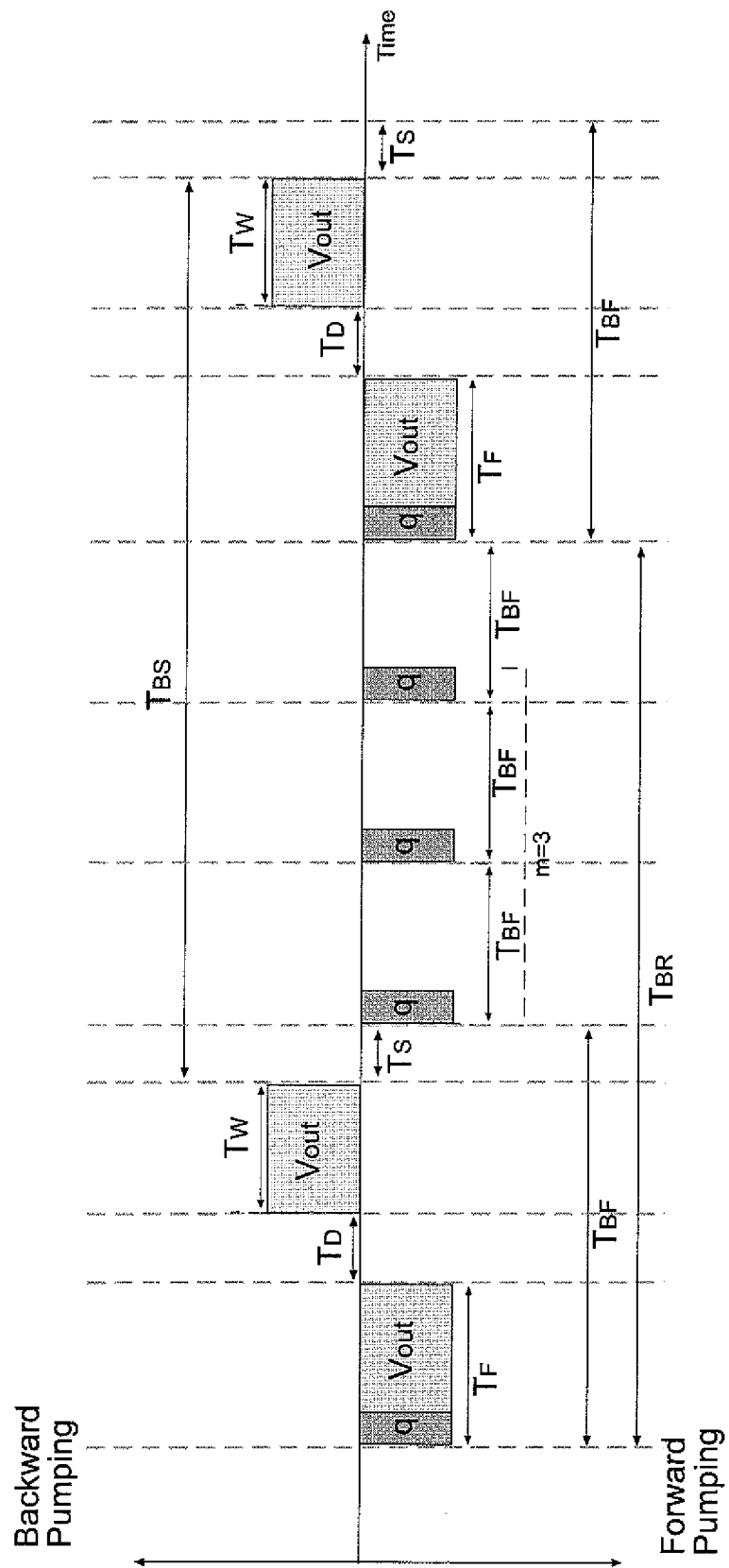
FIG. 23 are time diagrams of a reciprocating cycle with (a) three, (b) six, and (c) zero fluid delivery phases between two consecutive reciprocating cycles.
Figure 23B:
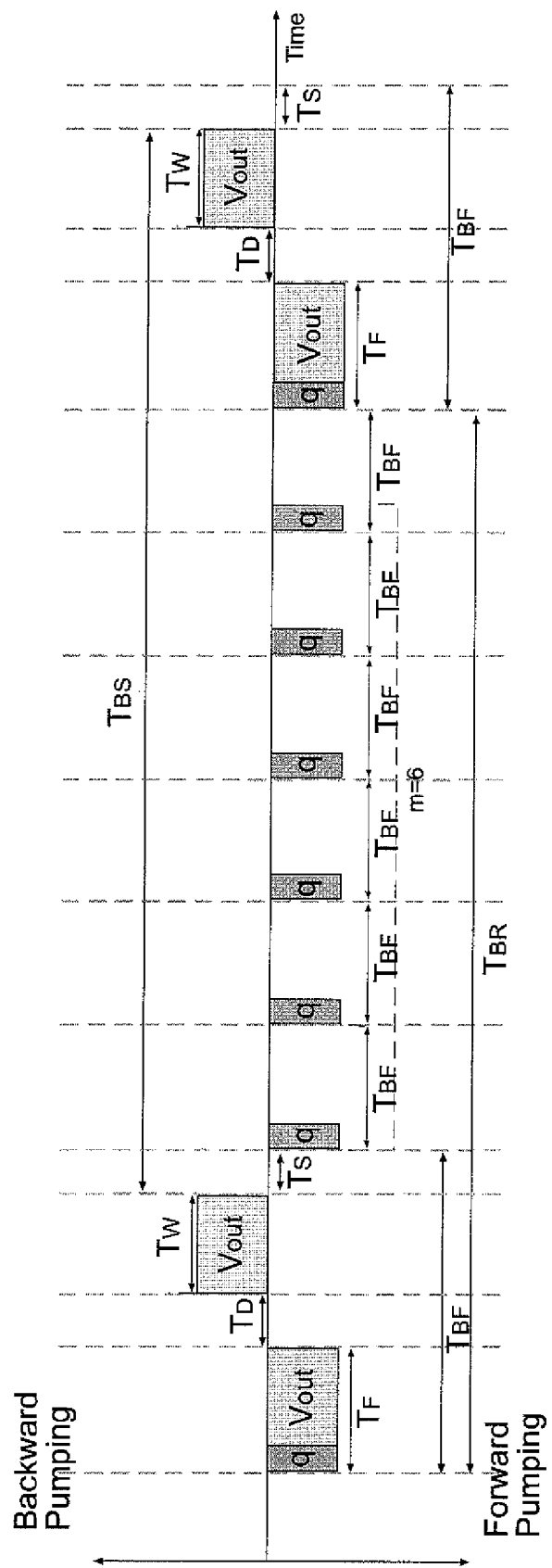
Figure 23C:
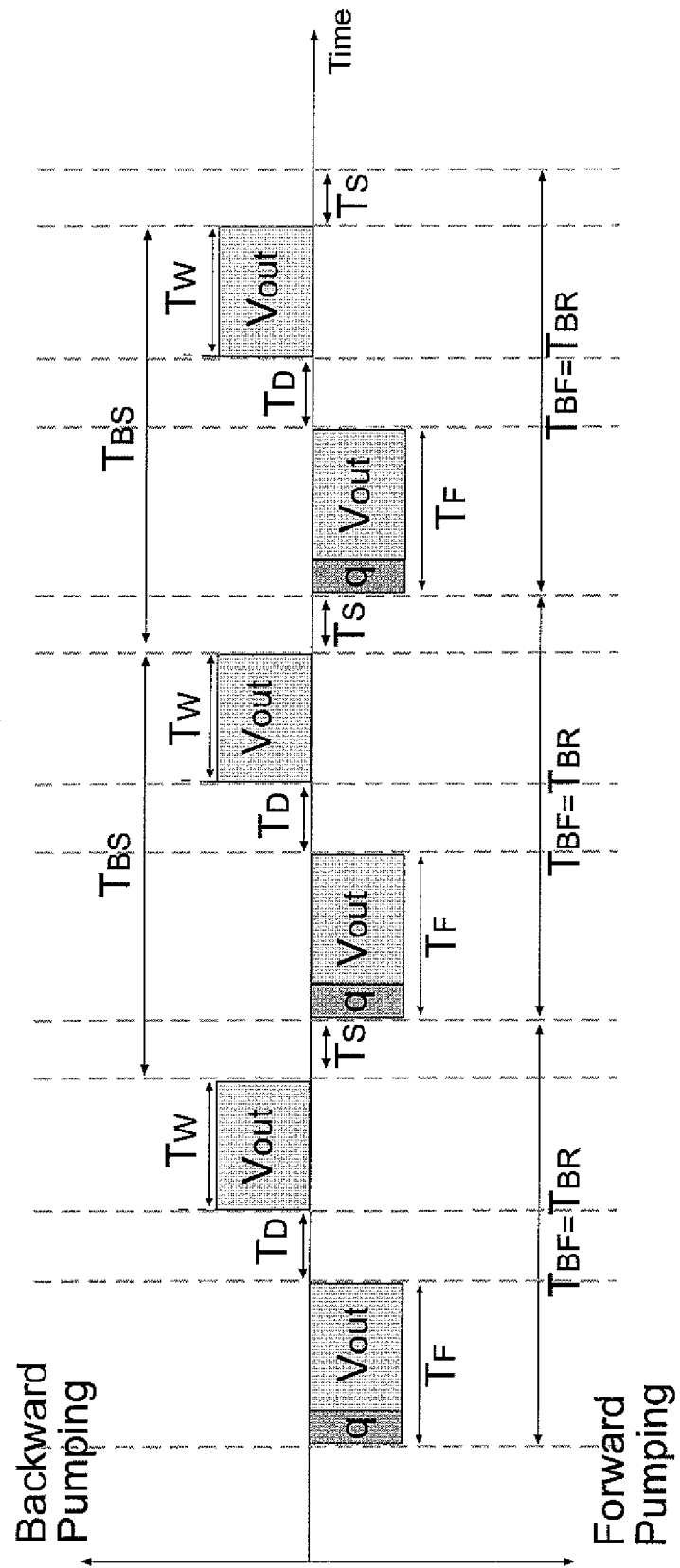

FIG. 23 shows a series of timelines representing sequences of forward and backward pumping during delivery and reciprocating cycles. In this figure m—is number of delivery cycles (m=1, 2, 3, . . . ) between reciprocating cycles. In FIG. 23a, three delivery cycles (m=3) occur between the two reciprocating cycles. In FIG. 23b, six delivery cycles (m=6) occur, between the two reciprocating cycles. In FIG. 23c, no delivery cycles (m=0) occur at all between the reciprocating cycles (consecutive reciprocating cycles). When m=0, or in other words when only consecutive reciprocating cycles occur, the time between two fluid delivery phases ($T_{BF}$) equals the time between two sensing phases ($T_{BS}$), or $T_{BF}=T_{BS}$. In addition, the time between reciprocating cycles equals the time between fluid delivery phases, or in other words $T_{BR}=T_{BF}$.

Given various parameters, like insulin basal rates ($B_R$), and a known cannula inner diameter (ID), and cannula length (h), below are several examples for calculations of the insulin volume required by the user ($V_R$), the length of tubing needed to delivery the volume required by the user (l), the volume of fluid pumped into the body during a fluid delivery phase ($V_{IN}$), and the volume of fluid pumped out of the body during a fluid withdrawal phase ($V_{OUT}$).

Figure 24:
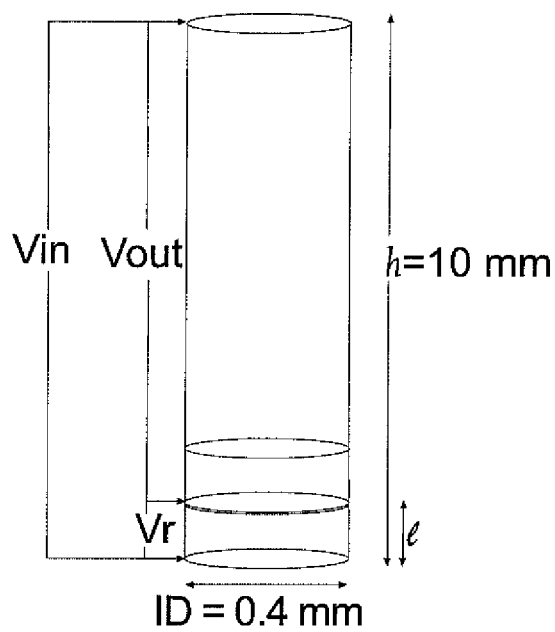
FIG. 24 is a schematic diagram showing a device that includes a tube that holds one quantum (q), and defined by a length l and an inner diameter ID.

FIG. 24 is a schematic drawing of a tube with length h and inner diameter ID. the basal rate ($B_R$) can I some examples be in a range from about 0.05 IU/h to 2.5 IU/h. In FIG. 24, the cannula inner diameter (ID) is 0.4 mm and the cannula length (h) is 10 mm. For purposes of this illustrative example, it is assumed that 100 IU (Insulin Units) are dissolved in 1 ml, and 1 IU is dissolved in 10 µl. Thus, the conversion between Insulin Units (IU) and volume (µl) is 1 IU=10 µl. Additionally, the pump is assumed to operate in a forward direction every 3 minutes. Therefore, $T_{BF}$, the time between fluid delivery phases is 3 min, and therefore there are 20 fluid delivery phases per hour.

The volume of insulin required by the user ($V_R$) is calculated according to the basal rate, $B_R$, needed by the user, the number of fluid delivery phases per hour, and the volume of insulin per IU. For example, given $B_R$=5 IU/h, 20 fluid delivery phases/hour, and 1 IU=10 µl, in each fluid delivery phase: (5 IU/h)/(20/h)=0.25 IU are pumped forward. Because $$V_R=0.25 \text{ IU} \times 10 \text{ µl/IU}=2.5 \text{ µl}, \tag{6}$$

$$V_R=B_R/20*10 \text{ µl}. \tag{7}$$

The length (l) of the tube needed to deliver $V_R$ is calculated according to $$l=V_R/\pi r^2 \text{ [mm]}, \tag{8}$$

the volume of fluid pumped out of the body during a fluid withdrawal phase ($V_{OUT}$) is calculated according to $$V_{OUT}=\pi(ID/2)^2 h=\pi(0.2)^2 h \text{ µl}, \tag{9}$$

and the volume of fluid pumped into the body during a fluid delivery phase ($V_{IN}$) is calculated according $$V_{IN}=V_{OUT}+V_R \tag{10}$$

Table 1 lists numerical examples for the calculation of various system parameters:

TABLE 1

Illustrative numerical examples for system parameters.

|  | I | II | III | IV | V | VI |
|---|---|---|---|---|---|---|
| Basal rate [IU/h] | 0.05 | 0.10 | 0.20 | 1.00 | 1.50 | 2.00 |
| ID [mm] | 0.4 | 0.4 | 0.4 | 0.4 | 0.4 | 0.4 |
| h [mm] | 10 | 10 | 10 | 10 | 10 | 10 |
| $V_R$ [µl] | 0.025 | 0.050 | 0.100 | 0.500 | 0.750 | 1.000 |
| l [mm] | 0.199 | 0.398 | 0.796 | 3.979 | 5.968 | 7.958 |
| $V_{OUT}$ [µl] | 1.257 | 1.257 | 1.257 | 1.257 | 1.257 | 1.257 |
| $V_{IN}$ [µl] | 1.282 | 1.307 | 1.357 | 1.757 | 2.007 | 2.257 |

Additional configurations for implementing devices according to the currently disclosed subject matter. For example, the device can include various cannula configurations, various fluid reservoir configurations, various pumping mechanisms, which provide various fluid dynamics between fluid delivery and fluid withdrawal.

FIG. 25 shows an embodiment of the fluid reciprocating system 1000, in which the cannula 6 is configured as a bifurcated element. One side of the bifurcated element is a dispensing arm 16, used for fluid dispensing and the other side of the fork, the sensing arm 166, is used for analyte sensing. Thus fluid delivery and analyte sensing are spatially separated. As shown in FIG. 25, a cannula 6 diverges into a dispensing arm 16 and a sensing arm 166. The fluid, which is stored in a reservoir 3, is pumped forward by a peristaltic pump 4 and delivered through the dispensing arm 16 and common arm 666 at the end of the cannula 6 into the body, and at the same time continues to be perfused backward through the sensing arm 166, to a sensing element 2000.

The sensing arm 166 can be semi or fully permeable. During the passage of the fluid through the sensing arm 166, analyte diffusion or other transport into the cannula interior volume occurs within the subcutaneous compartment 18, and partial or complete analyte concentration equilibrium can be established between the ISF analyte and the fluid within the sensing arm 166. Analyte concentration levels are measured by the sensing element 2000.

Figure 25A:
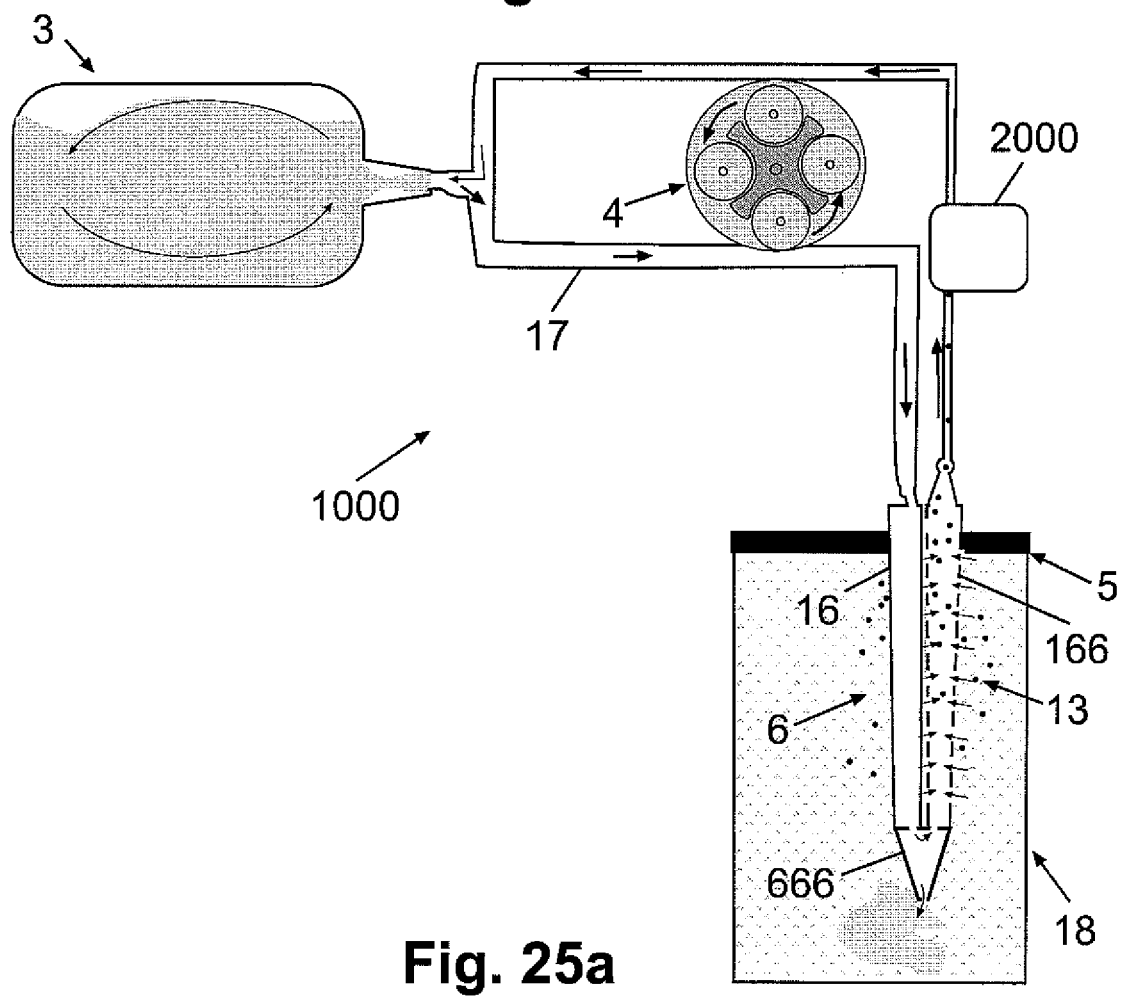
FIG. 25 are schematic diagrams showing a fluid reciprocating system with a forked cannula configured (a) to enable return of the analytic fluid to the reservoir and (b) as a unidirectional valve in which the analytic fluid cannot return to the reservoir.
Figure 25B:
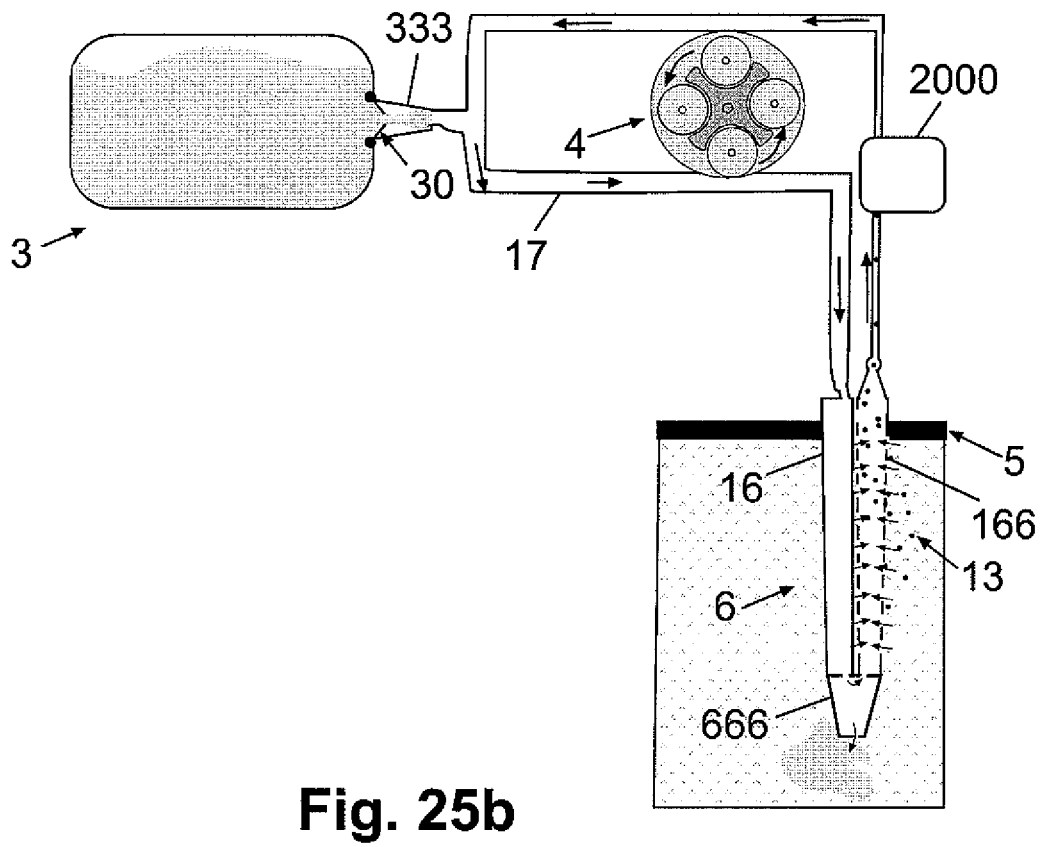

FIG. 25a shows an example implementation of a bifurcated cannula. After analyte sensing by the sensing element 2000, the fluid joins the analyte-free perfused fluid stored in the reservoir 3 and another reciprocating cycle begins. FIG. 25b shows another implementation in which a check valve, reverse flow restrictor, or other comparable regulation means 30, located at the reservoir outlet port 333, is provided. Thus, the analyte-rich perfused fluid, after passing through the sensing element 2000, is prevented from entering the reservoir 3 as it bypasses the reservoir 3 and instead enters the delivery tube 17.

In some implementations, the dispensing arm 16 through which fluid is pumped in a forward direction, can be impermeable. In other implementations, the dispensing arm 16 can be semi- or fully permeable, so that the diffusion or transport process occurs already at the dispensing arm 16, as shown in FIG. 26, and described below. The sensing arm 166 can have a smaller diameter than the dispensing arm 16, so that a portion of the fluid is delivered into the body through the common arm 666, and another portion of the fluid is pumped back through the sensing arm 166, to reach the sensing element 2000.

Because the diameter of the sensing arm 166 can be smaller than that of the dispensing arm 16, the fluid can be delivered to the body and its pumping rate can be controlled. The recovery generally depends on flow rate (for example on the insulin basal rate for a diabetes control mechanism). For example, if full recovery is achieved at a basal rate of 1 IU/h, only 80% recovery is achieved at basal rate of 0.5 IU/h because the diffusion equation is not linear a linear function.

Figure 26A:
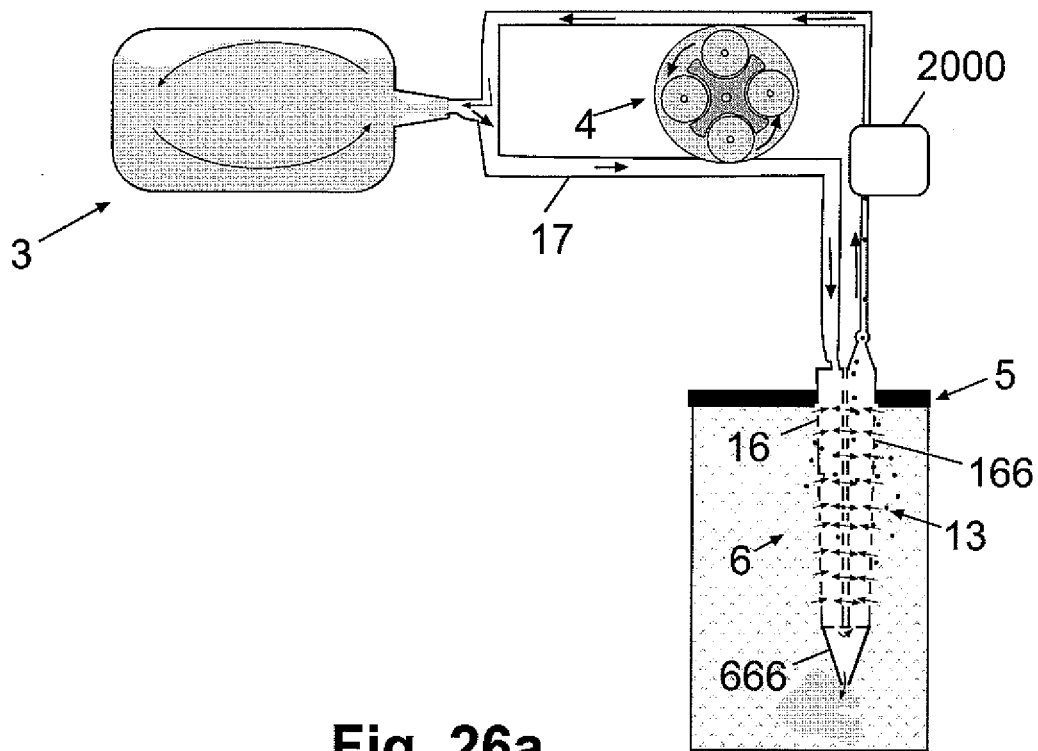
FIG. 26 are schematic diagrams showing fluid reciprocating systems with a forked cannula fitted with a semi or fully permeable dispensing arm.
Figure 26B:
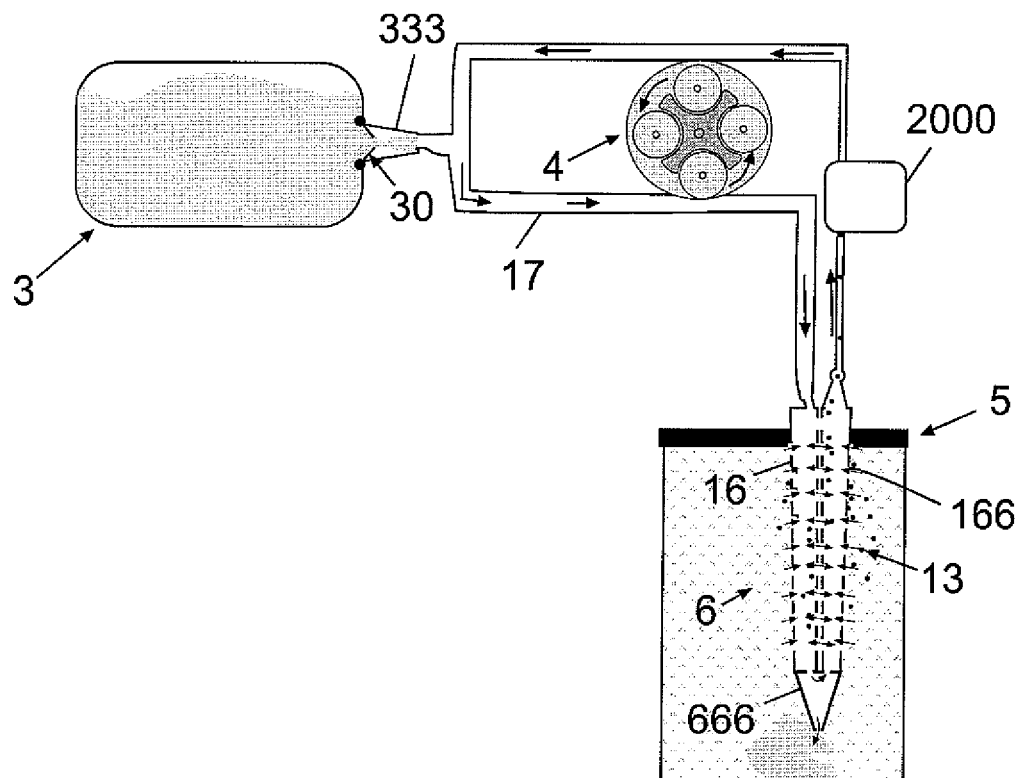

FIG. 26 shows another implementation in which both the dispensing and sensing arms 16,166 are semi or fully-permeable. Thus, analyte diffusion or transport into the fluid occurs during the fluid passage through both arms, thereby enhancing recovery. In this configuration, fluid recycling can be with returning the fluid into reservoir 3 as shown in FIG. 26a or without entering the reservoir due to the presence of a check valve 30 as shown in FIG. 26b.

Figure 27:
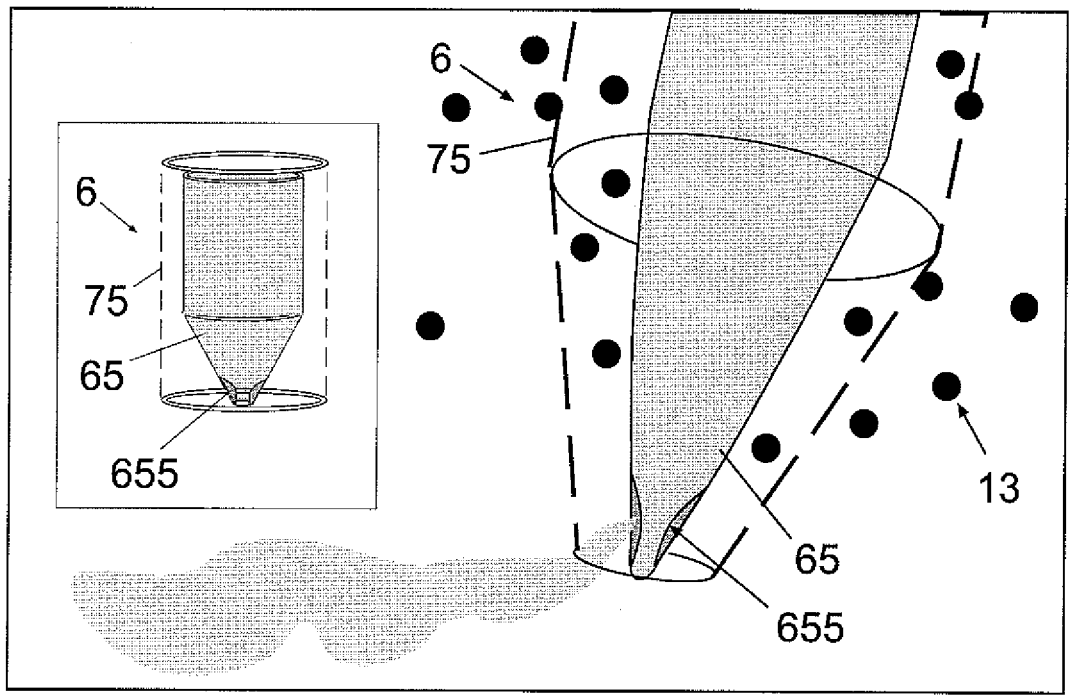
FIG. 27 is a schematic diagram showing a double lumen cannula.

FIG. 27 shows an example of a cannula that can be used for sensing analyte concentration levels and for delivering fluid. In this embodiment the cannula 6 is configured as two coaxial tubular elements, comprising an inner tube 65 and an outer tube 75. The inner tube 65 of the cannula 6 is used to deliver fluid and the outer tube 75 is used to deliver analyte-enriched fluid for sensing its concentration levels. In this case, the outer wall of the cannula 6 may be semi or fully permeable. The fluid may escape the inner tube, via the holes 655 at its tip. Analyte molecules 13 diffuse or are otherwise transported into and out of the cannula 6 via the semi or fully permeable outer tube 75.

Figure 28A:
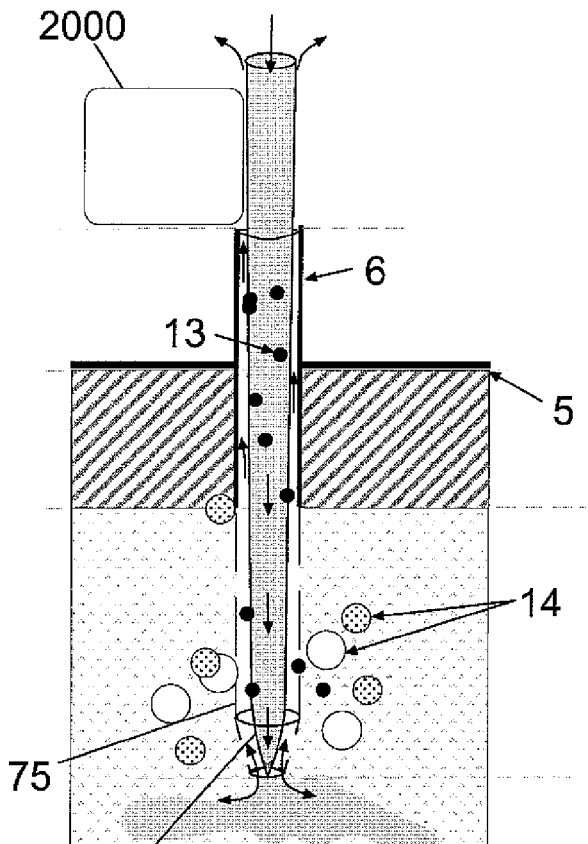
FIG. 28 are schematic diagrams showing a double lumen cannula with a (a) semi permeable and (b) permeable outer tube membrane.
Figure 28B:
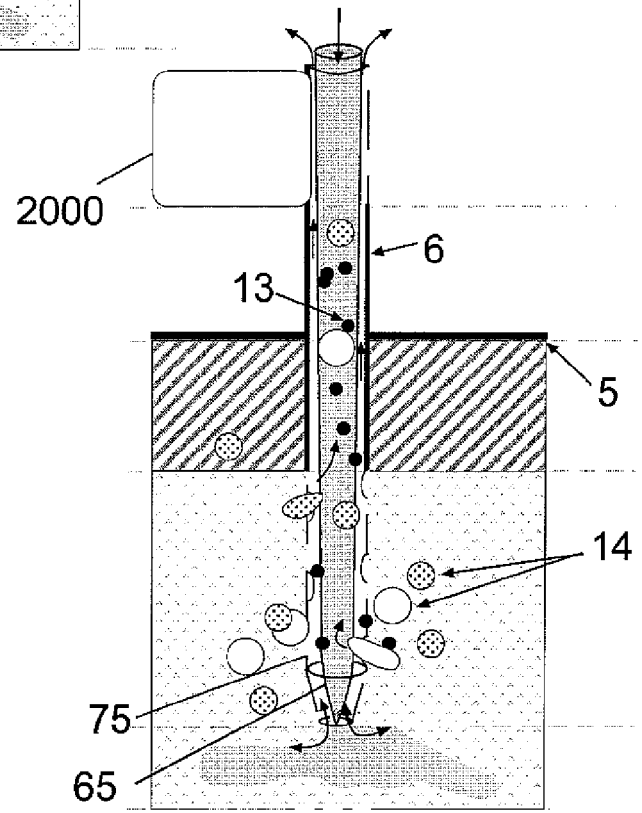

FIG. 28 shows examples of a coaxial cannula that can include an inner tube 65 within an outer tube 75, which constitutes a semi permeable (FIG. 28a) or permeable (FIG. 28b) outer membrane. The fluid (such as for example saline, insulin) can be delivered by the inner tube 65 to the body, while a portion of the fluid is transported back through the outer tube 75 (where analyte diffusion or other transport from the ISF occurs) towards the sensing element 2000 located above the skin surface 5. In FIG. 28a, the outer tube 75 is semi-permeable allowing for selective diffusion in which only small molecules 13 below the size of the membrane pores enter the cannula space. This is called microdialysis. When the outer tube 75 is fully permeable, as shown in FIG. 28b, non-selective diffusion occurs, and both small-size molecules, of the size of the desired analyte 13, and larger size molecules 14 enter the cannula space. This is called microperfusion, and it make reach an equilibrium state more quickly than by relying on diffusion alone.

FIG. 29 shows elements of a device that is provided with a fluid reciprocating system 1000. These elements include a coaxial cannula 6 having a dispensing arm 16 connected to an inner tube 65, and a sensing arm 166 connected to an outer tube 75. Fluid can be delivered by a pumping mechanism 4 from the reservoir 3, through the dispensing arm 16, via the inner tube 65 into the body, and backward via the outer tube 75, through the sensing arm 166 to the sensing element 2000, and back to the reservoir 3.

The inner tube 65 can be impermeable while the outer tube 75 can be fully permeable or semi-permeable allowing diffusion or similar analyte transport into the cannula. Diffusion or transport of analyte molecules occurs between the fluid that is perfused through the outer tube 75, and the ISF. Then the fluid is pumped upwards through the sensing arm 166 to a sensing element 2000 located above the skin surface 5, where measurement of the analyte-enriched fluid takes place. The perfused fluid, after passing through the sensing element 2000, either enters back into the reservoir 3 or proceeds to the delivery tube 17, due to a check valve 30 located at the reservoir outlet port 333 and preventing the analyte-enriched fluid from entering the reservoir 3. Alternatively, in another configuration, the dispensing arm 16 could be connected to the outer tube 75, which may be used for fluid delivery into the body, and the sensing arm 166 could be connected to the inner tube 65, which may be used for transporting of the analyte-enriched fluid to the sensing element 2000. The pumping mechanism 4 can be a peristaltic pumping mechanism, as shown, or some other type of suitable pumping mechanism.

FIG. 30 shows an implementation of a double-lumen cannula 6 in which the dispensing arm 16 and the sensing arm 166 are separated by a longitudinal wall. FIG. 30a shows a general view of the double-lumen cannula 6. FIG. 30b shows a cross-section of the double-lumen cannula 6. For example, this cannula 6 could be used instead of a bifurcated cannula.

Figure 31A:
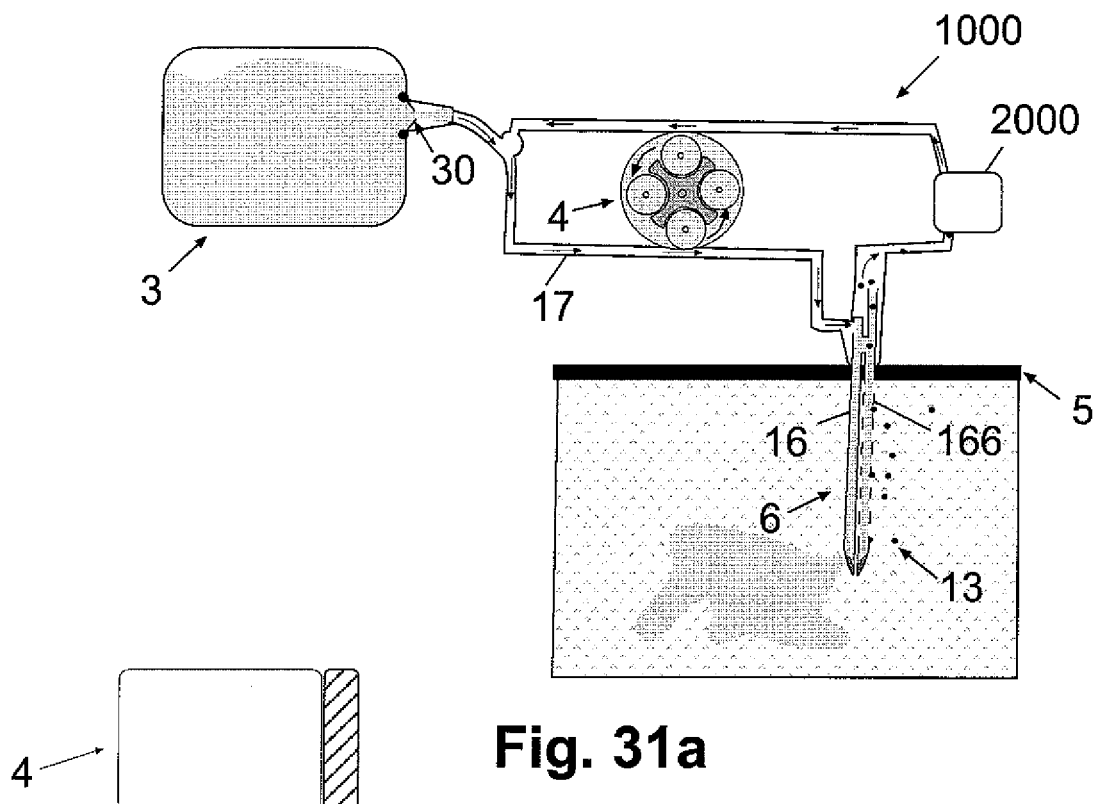
FIG. 31 are schematic diagrams showing a fluid reciprocating system fitted with a double lumen cannula, and provided either with (a) a peristaltic or (b) a syringe pumping mechanism.
Figure 31B:
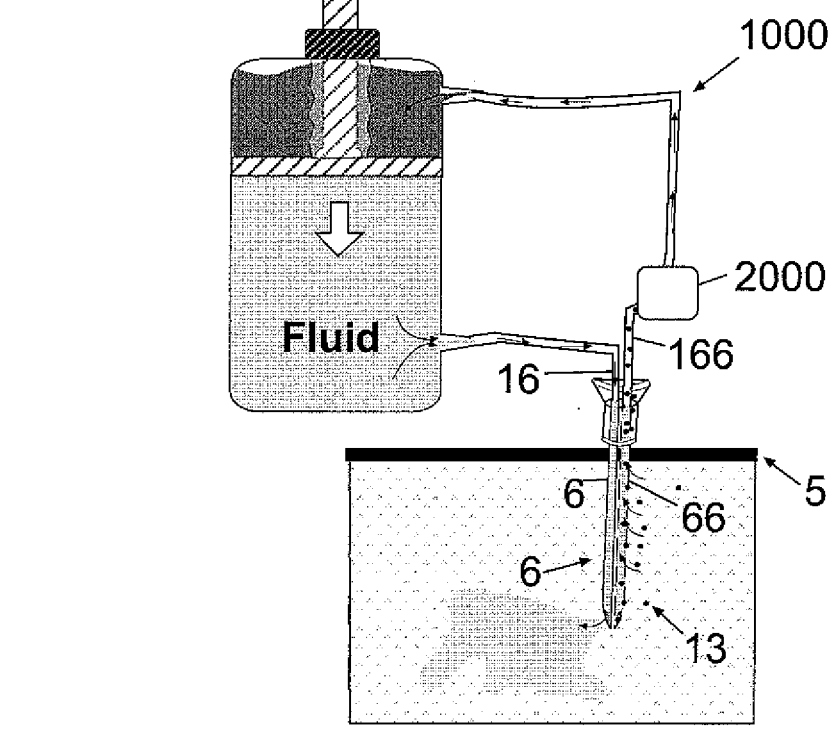

FIG. 31 shows another embodiment of the fluid reciprocating system 1000 fitted with a single double-lumen cannula 6. The longitudinal separation between the dispensing arm 16 and the sensing arm 166 allows for fluid (e.g. saline, insulin) delivery and analyte (e.g. glucose) sensing, respectively. Fluid from the reservoir 3 is pumped forward and delivered through the delivery tube 17, through the dispensing arm 16, into the body. Fluid-enriched analyte is transported backwards through a semi- or fully permeable sensing arm 166, to a sensing element 2000 and can be recycled with or without the reservoir fluid. The pumping mechanism 4 can be a peristaltic pumping mechanism, as shown in FIG. 31a, or for example a plunger pumping mechanism, as in FIG. 31b, or some other type of suitable pumping mechanism. In optional variations, the dispensing and sensing arms can be distributed among two cannulae that are insertable in parallel.

Figure 32:
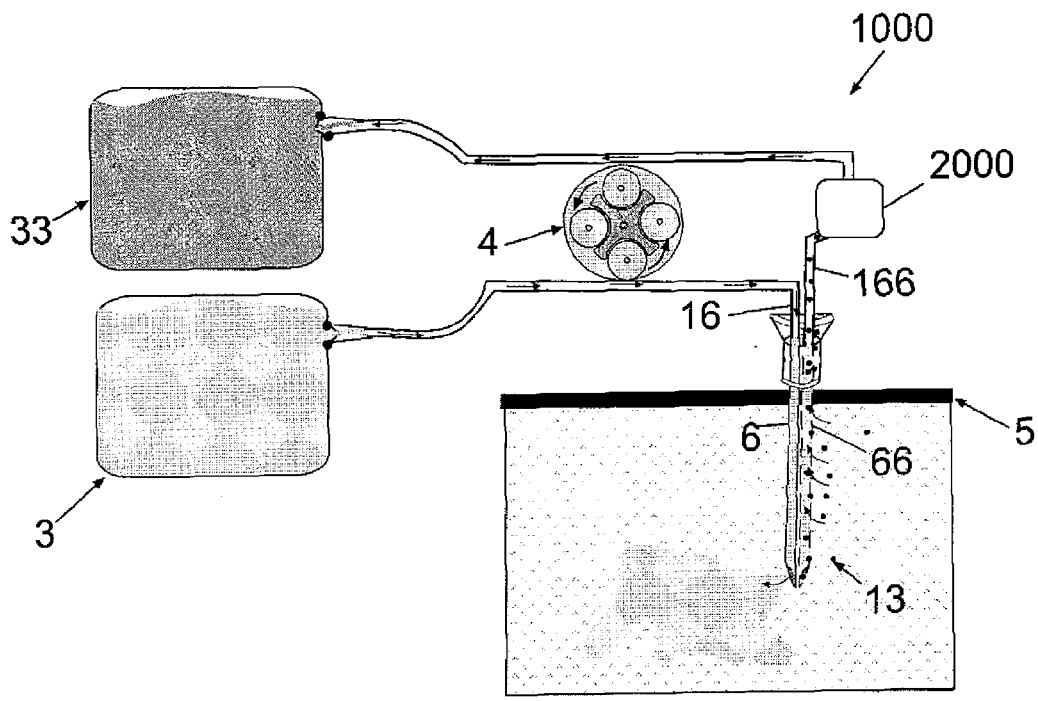
FIG. 32 is a schematic diagram showing a fluid reciprocating system in which dispensing and sensing apparatuses include separate cannulae and separate reservoirs.

FIG. 32 shows another implementation of a fluid reciprocating system 1000 in which the dispensing apparatus and the sensing apparatus share a common pumping mechanism 4, which can be a peristaltic pump. In FIG. 32, each apparatus comprises an independent cannula 6, 66 and an independent reservoir 3, 33. The same pumping mechanism 4 is used for pumping fluid forward, for example for dispensing, and for pumping fluid backward, for example for sensing. The pump 4 dispenses fluid from the reservoir 3 via the impermeable dispensing arm 16 through the dispensing cannula 6 into the body. After diffusion or transport from the ISF to the interior of the cannula 6, which can occur across a semi- or fully permeable membrane 66 of the sensing cannula, the analyte enriched fluid is delivered through the sensing arm 166 to the sensing element 2000 and collected in a waste reservoir 33. The pumping mechanism 4 can be a peristaltic pumping mechanism, as shown, or some other type of suitable pumping mechanism.

Figure 33:
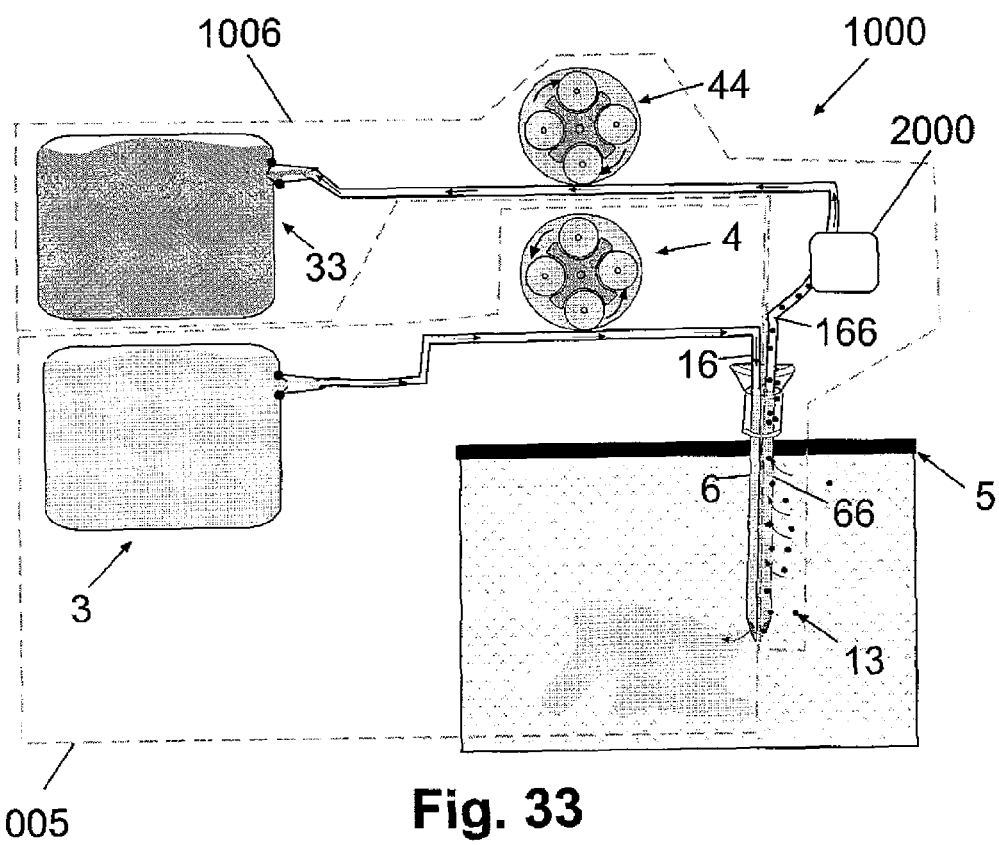
FIG. 33 is a schematic diagram showing a fluid reciprocating system in which dispensing and sensing apparatuses include separate cannulae, separate reservoirs, and separate pumping mechanisms.

FIG. 33 shows another implementation of a fluid reciprocating system 1000 in which the dispensing apparatus 1005 and sensing apparatus 1006 have separate reservoirs 33, 3, pumps 44, 4 and cannulae 66, 6. The dispensing apparatus pumps fluid from the reservoir 3 through the impermeable dispensing cannula 6 into the body. The sensing apparatus pumps 44 fluid from the body, through a semi- or fully permeable sensing cannula 66 to a waste reservoir 33. The pumping mechanism 4 can be a peristaltic pumping mechanism, as shown, or some other type of suitable pumping mechanism.

Figure 34:
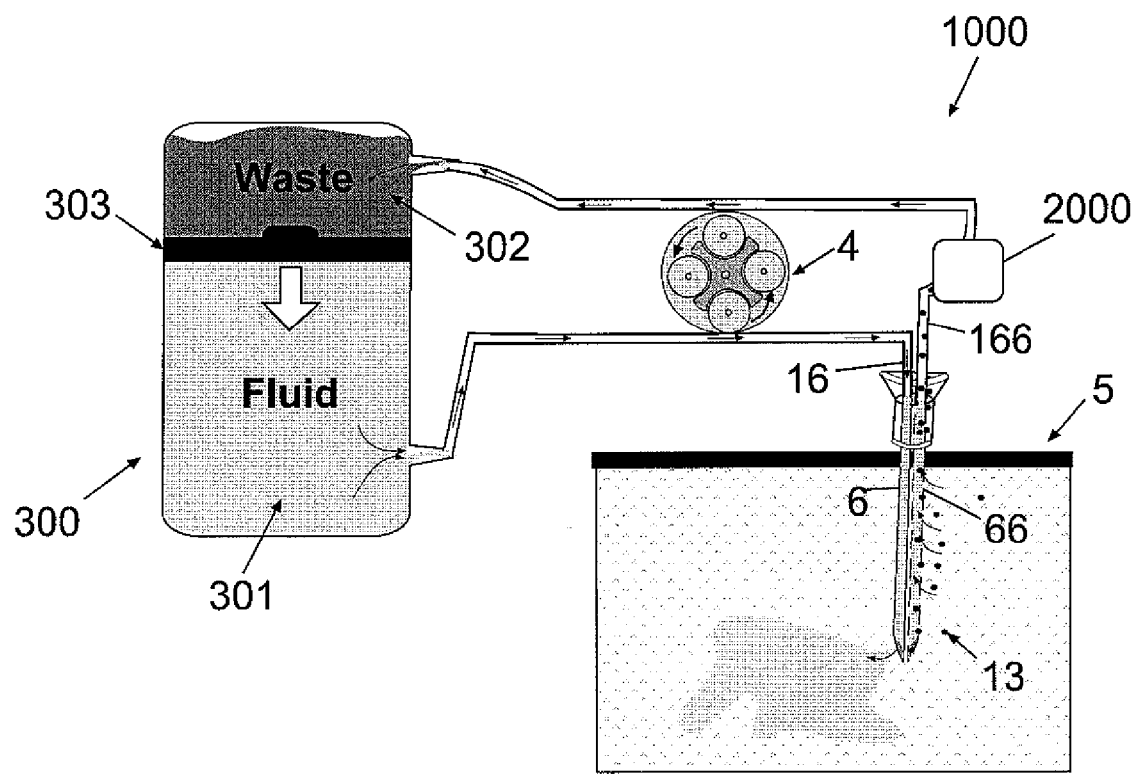
FIG. 34 is a schematic diagram showing a reciprocating system with a two-compartment reservoir

FIG. 34 shows a preferred embodiment of reciprocating system 1000 which contains a reservoir 300 divided into an analyte-free fluid compartment 301 and an analyte-enriched fluid compartment 302. The reciprocating system is fitted with a movable plunger 303. During the reciprocating cycle analyte-free and analyte-enriched fluids enter and leave the body and accordingly the analyte-free fluid exits from the compartment 301 and analyte-reached fluid enters the compartment 302.

The subject matter described herein may be embodied in systems, apparatus, methods, and/or articles depending on the desired configuration. In particular, various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

The implementations set forth in the foregoing description do not represent all implementations consistent with the subject matter described herein. Instead, they are merely some examples consistent with aspects related to the described subject matter. Wherever possible, the same reference numbers have been used throughout the drawings to refer to the same or like parts. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein do not require the particular order shown, or sequential order, to achieve desirable results. Other embodiments may be within the scope of the following claims.

What is claimed is:

1. A method comprising:
   delivering a volume of a therapeutic fluid from a reservoir in a patch unit into a subcutaneous compartment of a user via a first conduit and a cannula inserted within the subcutaneous compartment, the delivering occurring under the influence of a pumping mechanism in the patch unit that operates to displace the therapeutic fluid in a forward direction;
   suspending delivery of the therapeutic fluid by setting the pumping mechanism in a substantially static state such that the therapeutic fluid achieves at least a partial analyte concentration equilibrium with interstitial fluids in the subcutaneous compartment by transport of an analyte from interstitial fluids in the subcutaneous compartment to the therapeutic fluid;
   withdrawing at least part of the volume of the therapeutic fluid out of the subcutaneous compartment and into the patch unit via the cannula and a second conduit separate from the first conduit by operating the pumping mechanism to displace the at least part of the volume in a reverse direction;
   measuring an analyte concentration in the withdrawn volume using a sensing element within the patch unit; and
   providing regulation means for preventing the withdrawn volume from entering the reservoir while allowing the therapeutic fluid to exit from the reservoir.

2. A method as in claim 1, wherein the cannula comprises a permeable or semi-permeable surface through which molecules of the analyte diffuse during the substantially static state.

3. A method as in claim 1, wherein the cannula comprises a permeable surface through which molecules of the analyte microperfuse during the substantially static state.

4. A method as in claim 1, further comprising: initiating a change to a delivery rate of the therapeutic fluid based on the measured analyte concentration.

5. A method as in claim 1, further comprising: promoting a notification to a user interface, the notification requesting authorization of a proposed change to a delivery rate of the therapeutic fluid based on the measured analyte concentration.

6. A method as in claim 5, wherein the user interface is provided on a remote control unit that communicates with the patch unit, the remote control unit receiving fluid delivery programming commands.

7. A method as in claim 1, further comprising: converting the measured analyte concentration in the at least part of the volume of the therapeutic fluid to a calculated analyte concentration in the interstitial fluid or in a blood of the user.

8. A method as in claim 1, wherein the measuring of the analyte concentration occurs via electrochemical or optical sensing.

9. A method as in claim 1, wherein the therapeutic biologically compatible fluid comprises is insulin or saline.

10. A method as in claim 1, wherein the analyte comprises is glucose.

11. A method as in claim 1, further comprising;
delivering the withdrawn volume back into the subcutaneous compartment by operating the pumping mechanism to displace the withdrawn volume in the forward direction.

12. A method as in claim 1, wherein the patch unit comprises:
a disposable part that comprises the reservoir; and
a reusable part that comprises a control processor, at least part of a detector system, and at least part of the pumping mechanism, the patch unit being operable upon connection of the disposable part and reusable part.

13. A method as in claim 12, wherein one or more components of the detector system reside in each of the reusable part and the disposable part.

14. A method as in claim 12, wherein the patch unit is removably mated with a cradle unit that comprises a skin contact surface configured for contact with skin of the user.

15. A method as in claim 14, wherein a disposable cannula cartridge unit that comprises the cannula is configured for mating with the cradle unit to position a distal end of the cannula in the subcutaneous compartment and enabling communication of the therapeutic fluid between the reservoir and the subcutaneous compartment via the cannula.

16. The method as in claim 1, further comprising storing the withdrawn at least part of the volume of the therapeutic fluid in a waste reservoir.

17. The method as in claim 1, wherein, the regulation means comprises a check valve.

18. The method as in claim 1, wherein the regulation means comprises a reverse flow restrictor.

19. A patch unit for delivering a therapeutic fluid to a user and measuring a level of analyte in a user, the patch unit comprising:
a cannula having an insertable end configured for insertion into a subcutaneous compartment of the user;
a reservoir in fluid communication with the cannula, the reservoir comprising a therapeutic fluid;
a pumping mechanism that:
operates to displace the therapeutic fluid in a forward direction to deliver a volume of the therapeutic fluid from the reservoir into the subcutaneous compartment via a first conduit and the cannula,
suspends delivery of the therapeutic fluid to the subcutaneous compartment by entering a substantial static state such that the therapeutic fluid achieves at least a partial analyte concentration equilibrium with interstitial fluids in the subcutaneous compartment by transport of an analyte from interstitial fluids in the subcutaneous compartment to the therapeutic fluid, and
operates to displace the therapeutic fluid in a reverse direction to withdraw at least part of the volume of the therapeutic fluid out of the subcutaneous compartment and into the patch unit via the cannula and a second conduit separate from the first conduit,
a sensing element that measures an analyte concentration in the at least part of the volume of the therapeutic fluid withdrawn from the subcutaneous compartment; and
regulation means for preventing the withdrawn volume from entering the reservoir while allowing the therapeutic fluid to exit from the reservoir.

20. The patch unit as in claim 19, further comprising a waste reservoir for storing the withdrawn at least part of the volume of the therapeutic fluid.

21. The patch unit as in claim 19, wherein the regulation means comprises a check valve.

22. The patch unit as in claim 19, wherein the regulation means comprises a reverse flow restrictor.

* * * * *